United States Patent
Hugenroth et al.

(10) Patent No.: US 9,267,503 B2
(45) Date of Patent: Feb. 23, 2016

(54) ROTARY SYSTEMS LUBRICATED BY FLUID BEING PROCESSED

(71) Applicant: CAIRE Inc., Ball Ground, GA (US)

(72) Inventors: Jason James Hugenroth, Baton Rouge, LA (US); David Phillip Winter, Encinitas, CA (US); Raziel Alon, San Diego, CA (US)

(73) Assignee: Caire Inc., Ball Ground, GA (US)

( * ) Notice: Subject to any disclaimer, the term of this patent is extended or adjusted under 35 U.S.C. 154(b) by 0 days.

(21) Appl. No.: 14/248,148

(22) Filed: Apr. 8, 2014

(65) Prior Publication Data

US 2014/0219845 A1  Aug. 7, 2014

Related U.S. Application Data

(63) Continuation-in-part of application No. 12/879,998, filed on Sep. 10, 2010, now abandoned.

(60) Provisional application No. 61/241,331, filed on Sep. 10, 2009.

(51) Int. Cl.

| *F01C 1/00* | (2006.01) |
|---|---|
| *F04C 18/356* | (2006.01) |
| *F04C 23/00* | (2006.01) |
| *F04C 29/02* | (2006.01) |
| *B01D 53/047* | (2006.01) |
| *F01C 21/10* | (2006.01) |
| *F04C 18/32* | (2006.01) |
| *F04C 18/38* | (2006.01) |

(52) U.S. Cl.
CPC .............. *F04C 29/02* (2013.01); *B01D 53/047* (2013.01); *B01D 53/0476* (2013.01);
(Continued)

(58) Field of Classification Search
CPC B01D 53/047; B01D 53/0476; F01C 21/104; F04C 18/322; F04C 18/3564; F04C 18/38; F04C 23/001; F04C 29/02

USPC .......................... 418/241, 63, 64, 83, 105, 138
See application file for complete search history.

(56) References Cited

U.S. PATENT DOCUMENTS

| 993,530 A | 5/1911 | Kinney |
|---|---|---|
| 2,313,387 A | 3/1943 | McArthur et al. |

(Continued)

FOREIGN PATENT DOCUMENTS

| EP | 1640611 A1 | 3/2006 |
|---|---|---|
| EP | 1975412 A2 | 10/2008 |

(Continued)

OTHER PUBLICATIONS

PCT International Search Report and Written Opinion dated Jun. 1, 2012, for PCT application No. PCT/US2010/048528.

*Primary Examiner* — Thai Ba Trieu
*Assistant Examiner* — Dapinder Singh
(74) *Attorney, Agent, or Firm* — Fred C. Hernandez; Mintz Levin Cohn Ferris Glovsky and Popeo, P.C.

(57) ABSTRACT

Rotary systems are described, which can include at least one of compressors and vacuum pumps. Each rotary system includes a corresponding piston that rotates in an orbital motion around a respective eccentric of a shaft in order to either compress fluid or function as a vacuum pump. Multiple rotary systems can be executed on parallel on a single shaft such that these rotary systems are powered by a single motor. Various components of the rotary systems are coated with an abradable coating, which minimizes friction when these components come in contact with each other. The minimized friction minimizes the wear and tear of these components. Each rotary system can be lubricated by only the fluid being processed (for example, compressed or vacuumed) by that rotary system. The use of the fluid being processed for lubrication and the abradable coatings eliminate a need for another lubricant for lubricating the rotary system.

18 Claims, 35 Drawing Sheets

(52) U.S. Cl.
CPC ............ *F01C 21/104* (2013.01); *F04C 18/322* (2013.01); *F04C 18/3564* (2013.01); *F04C 18/38* (2013.01); *F04C 23/001* (2013.01); *F04C 2230/91* (2013.01)

(56) References Cited

U.S. PATENT DOCUMENTS

| | | | | |
|---|---|---|---|---|
| 2,536,851 | A | * | 1/1951 | Latham, Jr. ................ 418/91 |
| 3,073,118 | A | * | 1/1963 | August ...................... 123/213 |
| 3,102,516 | A | * | 9/1963 | Gist et al. .................... 418/83 |
| 3,279,442 | A | * | 10/1966 | Birk ............................ 123/1 R |
| 3,521,981 | A | | 7/1970 | Krzyszczuk |
| 3,769,944 | A | * | 11/1973 | Raymond .................. 123/235 |
| 2008/0107556 | A1 | * | 5/2008 | Bae et al. ..................... 418/63 |
| 2008/0193314 | A1 | | 8/2008 | Cho et al. |
| 2011/0058970 | A1 | | 3/2011 | Hugenroth |

FOREIGN PATENT DOCUMENTS

| | | |
|---|---|---|
| JP | 58085389 A | 5/1983 |
| WO | WO-2009037968 A1 | 3/2009 |

\* cited by examiner

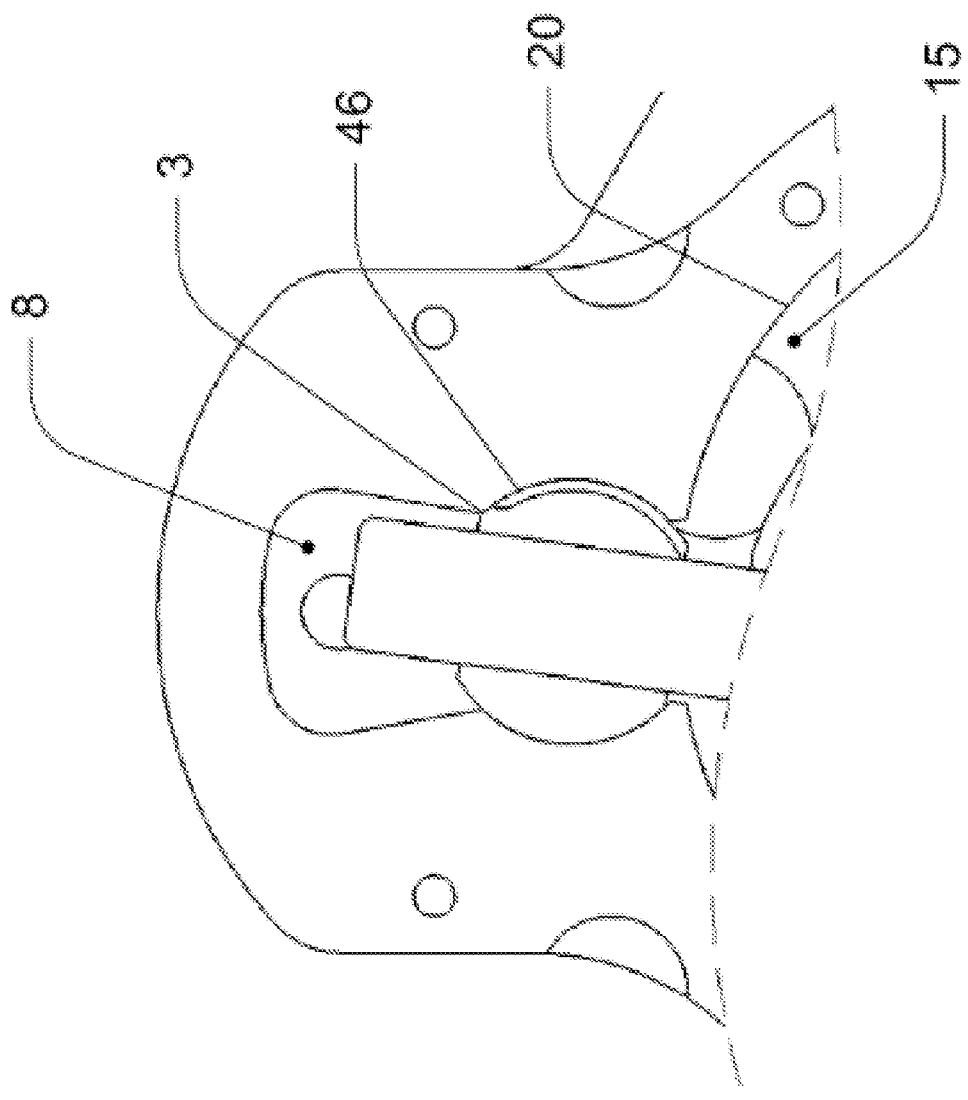

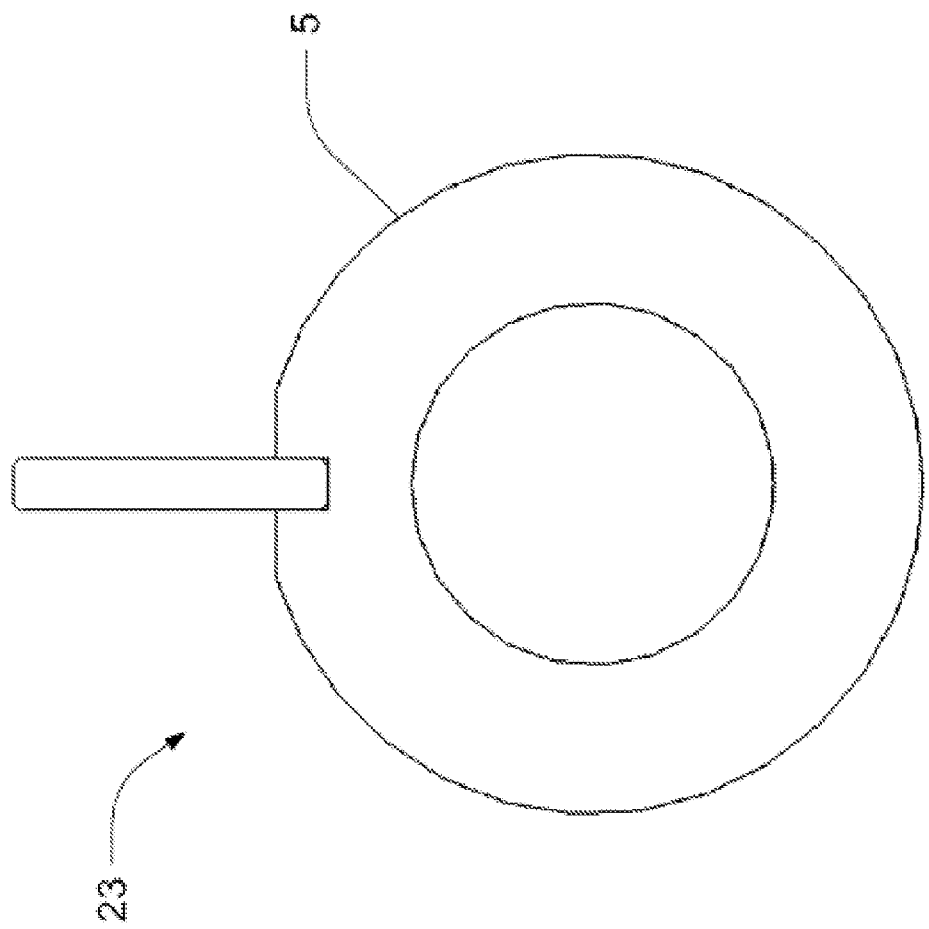

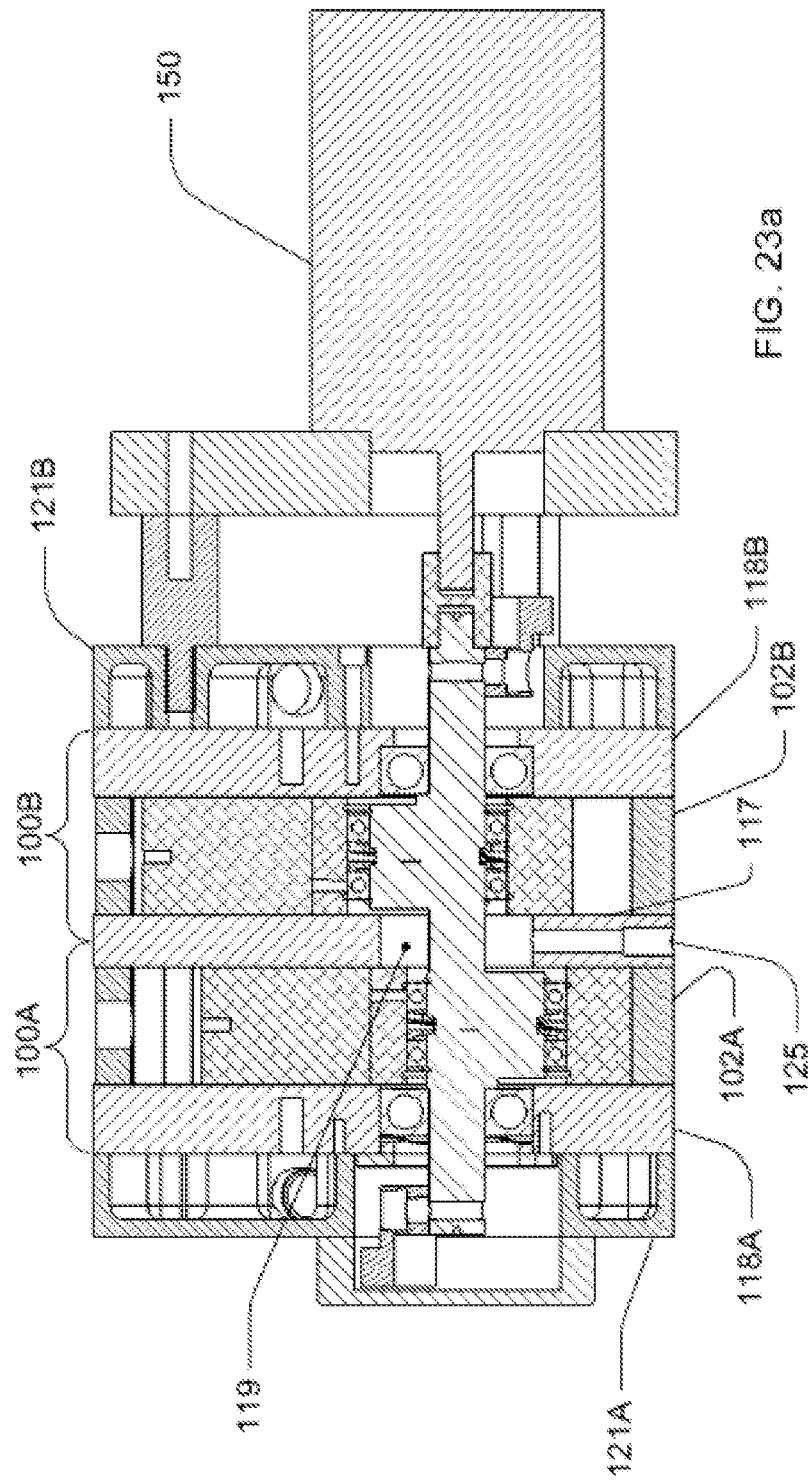

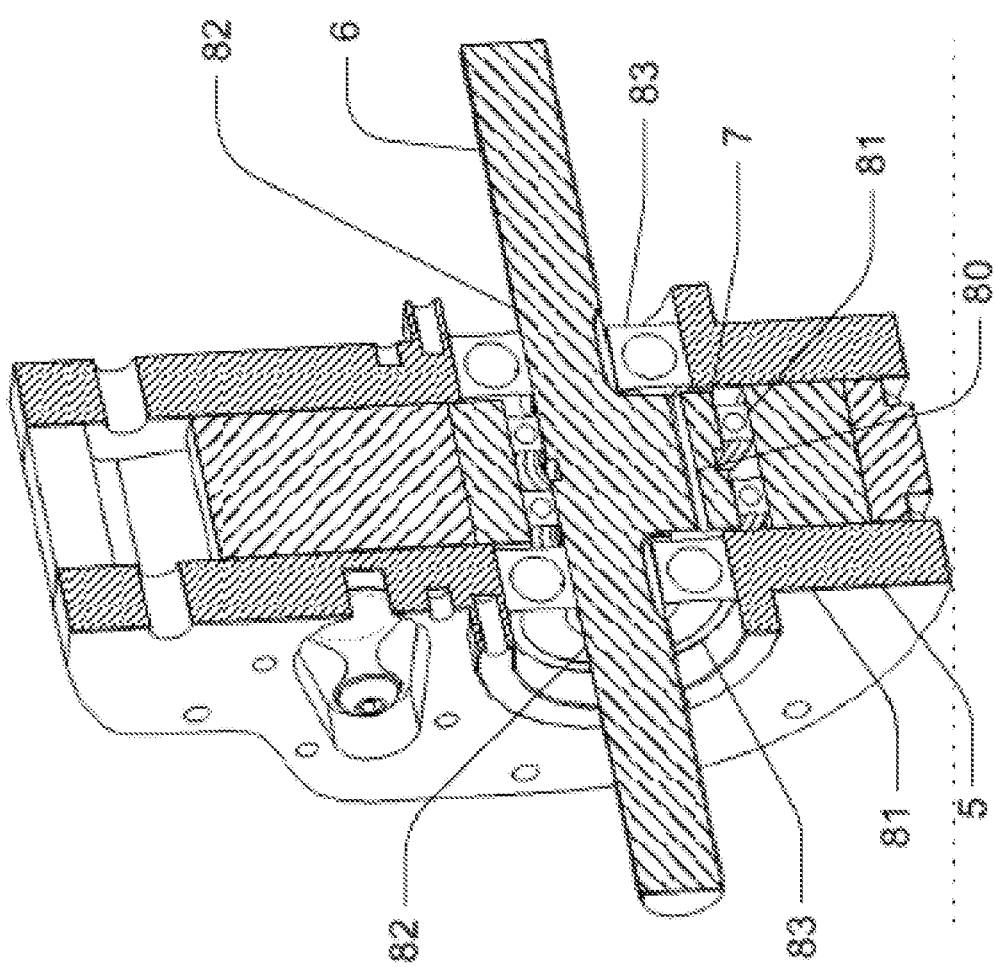

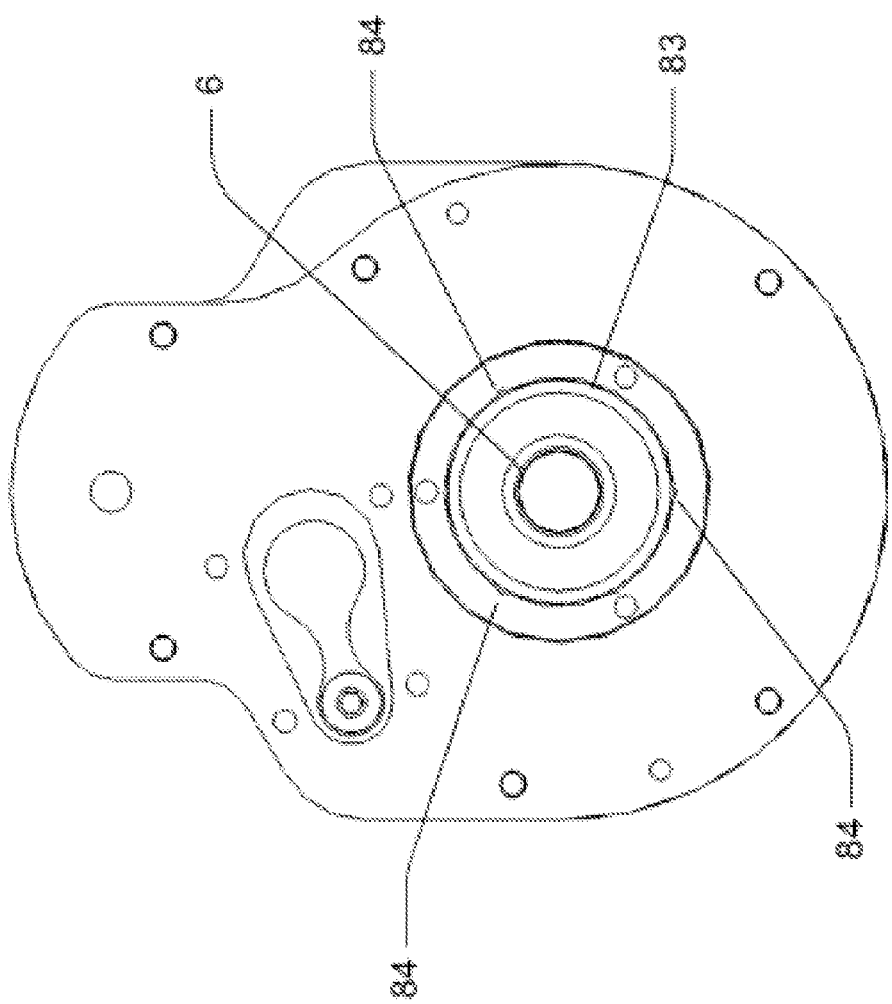

ROTARY SYSTEMS LUBRICATED BY FLUID BEING PROCESSED

RELATED APPLICATIONS

This application claims priority to U.S. patent application Ser. No. 12/879,998, entitled "Rotary Compressor and Method," and filed Sep. 10, 2010, which further claims priority to U.S. Provisional Patent Application Ser. No. 61/241,331, entitled "Rotary Compressor and Method," and filed Sep. 10, 2009. The content of the above-mentioned applications is incorporated by reference in entirety.

TECHNICAL FIELD

The subject matter described herein relates to rotary systems, which can include at least one of rotary compressors and rotary vacuum pumps. More specifically, each rotary system includes a corresponding piston that rotates in an orbital motion around a respective eccentric of a shaft in order to either compress incoming fluid or function as a vacuum pump.

BACKGROUND

U.S. Pat. No. 993,530 and U.S. Pat. No. 2,313,387 disclose rotary compressors. Compressors configured in this manner are commonly used as vacuum pumps and as refrigeration compressors. Liquid lubricants perform several functions within a compressor. Lubricants reduce the friction between contacting components that are in relative motion with respect to one another. This reduces frictional heating and wear. For example, surrounding the compression space of a compressor small leakage paths exist between adjacent parts that allow compressed gas at a relatively high pressure to leak to low pressure areas. This reduces the efficiency of the compressor. Liquid lubricants are able to effectively seal these leakage paths, thus, increasing efficiency.

In addition, the specific thermal capacitance of liquids is much higher than that of gases. Therefore, relatively small amounts of liquid lubricant in the compression space are able to absorb a relatively large amount of heat. When a gas is compressed adiabatically a substantial temperature rise of the gas occurs. During operation of a lubricated compressor, liquid lubricant, in the compression space can absorb some of the heat-of-compression. This decreases the temperature rise of the gas being compressed. Because compression work is directly proportional to gas temperature, the efficiency of the compressor is improved.

Liquid lubricants can also bear substantial loads, such that parts that appear to contact are actually separated by a thin film of lubricant even when the force trying to bring the parts into contact is substantial. Gases, on the other hand, support relatively small loads due to their low viscosity and high compressibility. Gases also leak much more readily from very small clearances.

In view of the benefits attributed to liquid lubricants in compressors, it becomes difficult to design an oil-less compressor that is efficient, reliable and cost effective to manufacture. Additionally, typical compressors suffer from other deficiencies that make them inefficient and noisy, they require increased power, and are subject to wear. The rotary compressors described herein solve these and other such issues.

SUMMARY

The current subject matter describes rotary systems, which can include at least one of compressors and vacuum pumps. Each rotary system includes a corresponding piston that rotates in an orbital motion around a respective eccentric of a shaft in order to either compress fluid or function as a vacuum pump. Multiple rotary systems can be executed in parallel on a single shaft such that these rotary systems are powered by a single motor. Various components of the rotary systems are coated with an abradable coating, which minimizes friction when these components come in contact with each other. The minimized friction minimizes the wear and tear of these components. Each rotary system can be lubricated by only the fluid being processed (for example, compressed or vacuumed) by that rotary system. The use of the fluid being processed for lubrication and the abradable coatings eliminate a need for another lubricant for lubricating the rotary system.

In one aspect, a system can include a first inlet, a first piston, and a first outlet. The first inlet is configured to receive fluid that is to be compressed. The first piston is configured to rotate around a first eccentric of a shaft in an orbital fashion in order to compress the fluid. The first piston is coated with an abradable coating. The fluid is used as a lubricant for lubricating the first piston. The use of the fluid for lubricating and the abradable coating eliminates a need of another lubricant (for example, oil or any other oil-like lubricant) for lubricating the first piston. The first outlet is configured to discharge the compressed fluid.

In some variations, one or more of the following can be implemented either individually or in any suitable combination. The system further includes a first vane connected to the first piston, a first set of bushings slidingly connected to the first vane, and a first stator configured to enclose the first piston and the first vane. The system can further include a suction endplate that incorporates the first inlet, and a discharge endplate that incorporates the first outlet. The first stator is coated with the abradable coating. In some implementations, the suction endplate and the discharge endplate are also coated with the abradable coating. In alternate implementations, the suction endplate and the discharge endplate may not be coated with the abradable coating. In most implementations, only one of two adjoining surfaces can be coated with the abradable coating. For example, only one of piston and the adjoining stator wall may be coated. The abradable coating minimizes friction between the first piston and the first stator. The minimized friction between the first piston and the first stator eliminates the need of another lubricant for lubricating the first piston. The abradable coating is at least one of a paint coating and a polymer based coating. Each bushing of the first set of bushings has a flat surface in contact with a surface of the first vane. The first stator encloses a chamber that includes at least a vane chamber and a bore chamber. The bore chamber includes a compression chamber and a suction chamber that is sealed from the compression chamber by the first vane and the first set of bushings. The compression chamber and the suction chamber are interchanged during the rotation of the first piston such that the compression chamber performs suction and the suction chamber performs compression.

The fluid that is to be compressed is ambient air. The ambient air is received at the first inlet from an ambient air collecting source. The ambient air includes oxygen, nitrogen, argon, and/or other gases. The compressed fluid is pressurized ambient air. The pressurized air goes from the first outlet to a separator device that separates the pressurized air into the oxygen, the nitrogen, the argon, and/or other gases. The separator device can be a vacuum-pressure-swing-adsorption (VPSA) device. In an alternate implementation, the separator device can be a pressure-swing-adsorption (PSA) device. In another implementation, the separator device can be a vacuum-swing-adsorption (VSA) device.

The system can further include a second inlet, a second piston, and a second outlet. The second inlet is configured to receive, from a separator device, exhaust gases that have been separated from the fluid. The one or more gases can be a subset of gases forming the fluid. The second piston is configured to rotate around a second eccentric of the shaft in the orbital fashion. Axial surfaces of the second piston are parallel to axial surfaces of the first piston. The second piston is coated with the abradable coating. The exhaust gases are used as a lubricant for lubricating the second piston. The use of the exhaust gases for lubricating and the abradable coating of the second piston eliminate a need of another lubricant for lubricating the second piston. The second outlet is configured to exhaust the gases.

The system can further include a second vane connected to the second piston, a second set of bushings slidingly connected to the second vane, and a second stator configured to enclose the second piston and the second vane. The first stator and the second stator can be a single machined unit. Locations of at least one of the first inlet and the second inlet can be moved to adjust timing of beginning of compression cycle for compressing the fluid.

An inner radial surface of the first piston can be connected to an outside surface of the first eccentric by a plurality of bearings. The plurality of bearings can be configured to float underneath the first piston until the piston is at a stable location with respect to the plurality of bearings where least amount of forces act upon the piston. The plurality of bearings can be at least one of rolling bearings (also referred to as roller bearings) and needle bearings.

In another aspect, ambient air is received at a first inlet of a rotary compressor powered by a motor. A first piston of the rotary compressor is rotated around a first eccentric of a shaft in an orbital motion to compress the ambient air into compressed gas. At a first outlet of the rotary compressor, the compressed gas is sent to a separator configured to separate the compressed gas into oxygen and other gases, such as nitrogen and argon. The rotary compressor is lubricated by the ambient air and the compressed gas while not requiring an oil-like lubricant. At a second inlet of a vacuum pump powered by the motor, the other gases are received from the separator. The vacuum pump includes a second piston configured to rotate around a second eccentric of the shaft in the orbital motion. The second piston is parallel to the first piston. The second eccentric has a radial diameter larger than the radial diameter of the first eccentric. The other gases are exhausted at a second outlet of the vacuum pump. The vacuum pump is lubricated by the other gases while not requiring the oil-like lubricant.

Another aspect of the present disclosure involves a rotary compressor that is primarily optimized for use without the need for liquid lubricants, such as in the flow path of the fluid being compressed. The compressors described herein are efficient, run quietly, use less power, and last longer than those previously known in the art. The compressors are useful for medical applications and other clean gas applications, for example, where lubricants could contaminate the fluid being compressed and/or increased noise and/or vibration may be problematic. A specific example being medical respiratory applications, such as, pressure-swing-absorption and vacuum-pressure-swing-absorption oxygen concentrators. The usefulness of the compressors described herein is not limited to traditional clean gas applications. For example, the lubricating oil used in refrigeration compressors coats the inside surfaces of the heat exchangers in the refrigeration system. This reduces the effectiveness of the heat exchangers, which results in a decrease in system efficiency. Use of the disclosed compressor technology in refrigeration systems could improve the efficiency of these systems.

The present rotary compressor is efficient, reliable, and cost effective to produce. Various implementations of the present disclosure permit the compressor to operate; without lubricating liquids, such as oil (or any other oil-like lubricant), on the surfaces contacted by the fluid being compressed or pumped; with reduced leakage; without contact between components or with reduced wear when contact does occur. Additional implementations are provided so as to increase efficiency, decrease vibrational noise and power requirements and increase durability.

Accordingly, provided herein, in a first aspect, is a rotary compressor for processing a fluid, such as for use in a fluid concentrator or refrigeration system. The compressor includes a housing, e.g., a stator element. The housing includes a plurality of surfaces that are axially separated surfaces that bound a chamber. The chamber may have multiple portions therein. For example, the chamber may have one, two, three, or more chamber portions. For example, one chamber portion may form a vane chamber, another portion may form a bushing chamber, and a further portion may form a cylinder chamber, e.g., a bore chamber portion. These chamber portions may be individual chamber portions, or in certain implementations, the chamber portions may be combined with one another to form a combined chamber portion. For example, in some implementations, the vane and bushing portions may be the same chamber portion. The housing itself is bounded. The housing may be bounded by one or a plurality of endplates, which may be disposed one on each of the axially separated surfaces of the housing thereby effectively sealing the chamber of the housing.

The housing may additionally include a cylindrical piston. In certain implementations, the piston may have opposing surfaces and include an interior diameter and an exterior diameter. The piston may be operatively associated with a drive member, such as a shaft, magnetic coupling, or the like. The piston may be disposed within the cylinder chamber portion of the housing and rotatable therein. In certain implementations, the piston may be offset with respect to a centerline of the cylinder chamber, e.g., bore chamber, portion, such that the outer diameter of the piston is in close proximity to the bounds of the cylinder chamber portion during rotation of the piston. For example, where a shaft is included the piston may be offset with respect to a centerline of the shaft. Accordingly, the piston in its orbit therefore may divide the cylinder chamber portion into a suction chamber sub-portion and a compression chamber sub-portion. Additionally, in some implementations, the piston is further associated with a vane member.

The housing may further include an elongated vane member. The vane member may be an extended member having a proximal portion, e.g., associated with the piston, and a distal portion. The vane member may be slidingly disposed within the chamber such that as the piston orbits within the cylinder, e.g., bore, chamber portion, the distal portion of the vane member extends at least partially into the bushing chamber portion, and/or vane chamber portion, if included.

The housing may additionally include at least one bushing, rotatably disposed in the bushing chamber, and a drive member for driving the piston in a rotational motion such that as a volume of the suction chamber increases a volume of the compression chamber decreases. The drive member may be any suitable drive member, such as a shaft connected to a drive motor, a magnetic coupling, and the like.

In some implementations, a rotary compressor of the disclosure does not have a fluid lubricant other than the process fluid within contact of the chamber. For example, for the purpose of increasing the efficiency of compressor function.

In other implementations, the rotary compressor may include a vane chamber, such as a vane chamber that is in fluid communication with the cylinder chamber portion, for a first portion of the piston's orbit, and may further be isolated from the cylinder chamber portion, for a second portion of the piston orbit, so as to reduce compressor power consumption and limit wear.

In one implementation, the piston and vane combination are balanced. The piston and vane combination are balanced when their composite center of mass is substantially coincident with the piston's orbit circle, wherein the orbit circle's center point is substantially coincident with the bore chamber centerline. In general, a cylindrical piston, separate from the vane, would be balanced. The presence of the vane on the piston makes the piston and vane combination unbalanced. The piston and vane combination are considered substantially balanced when at least a portion of the imbalance caused by the presence of the vane is reduced, i.e., when the root mean square of the perpendicular distance from the center of mass of the piston and vane combination to the orbit circle is reduced. For example, the piston may include a cutout portion, which cut out portion may form a chamber, which chamber may or may not be in communication with one or more of the bore chamber sub-chambers and/or a surface of one or more of the endplates.

In certain implementations, a bushing chamber may be included wherein the bushing chamber includes one or more bushings, such as, wherein the one or more bushings are rotatably disposed within the bushing chamber and the vane is slidingly disposed between a slot formed by the bushing. Where a plurality of bushings are provided, at least one of the bushings may include a recess, such as a recess that allows communication between the vane chamber and one or more chambers of the bore chamber, e.g., the suction or compression chambers. One or more bushing bearings may also be present in the bushing chamber, such as between the bushing and the bushing chamber surface.

In certain implementations, a dual cylinder rotary compressor is provided. The compressor may include a first housing having axially separated surfaces. The first housing may bound a chamber. The chamber may have multiple portions therein, such as portions that may include one or more of: a vane chamber portion, a bushing chamber portion, and a cylinder chamber portion. The compressor may additionally include a second housing having axially separated surfaces. The second housing may also bound a chamber. The chamber may have multiple portions therein, such as portions that may include one or more of: a vane chamber portion, a bushing chamber portion, and a cylinder chamber portion.

A plurality of endplates may also be included. The endplates may be disposed one on each of the axially separated surfaces of the housings thereby effectively sealing the chambers, wherein each housing shares at least one endplate. The shared endplate may have a generally axially aligned hole there through.

A drive mechanism, such as an elongated shaft may also be present and extend through the cylinder chamber portions of the first and second housings. The shaft may define a centerline therein and may be associated with a piston in each housing. A plurality of cylindrical pistons one of which is associated with the first housing another one of which is associated with the second housing may also be present.

The pistons may each have an interior diameter and an exterior diameter. They may be operatively associated with the drive mechanism, e.g., the shaft, the pistons being 180 degrees opposed to one another and offset from a centerline of the bore chamber such that the outer diameter of each piston is in close proximity to the bounds of the cylinder chamber portion of the housings, thereby dividing the cylinder chamber portions into a suction sub-chamber and a compression sub-chamber.

Each piston may further be associated with a vane member. Accordingly, a plurality of elongated vane members may be included. Each vane member may have a proximal portion that is associated with a respective piston and a distal portion, wherein each vane member is slidingly disposed within the respective chamber of the housings such that as the piston rotates within the cylinder chamber portion, the distal portion of the vane member extends at least partially into a bushing and/or vane chamber portion.

A plurality of bushings may also be included wherein the bushings may be rotatably disposed in each of the bushing chamber portions of the housings. The bushings may be configured such that the distal portion of each vane member is disposed between a slot formed by the bushings. The housings may additionally include a plurality of suction ports wherein each is in fluid communication with a suction chamber and/or a discharge port, such as in the compression chamber of each of the housings. A plurality of valve mechanisms for selectively controlling fluid communication between the compression chambers and the discharge ports may also be included.

A drive mechanism, such as a shaft coupled to a drive motor, for driving both of the pistons in a rotational motion may also be provided.

In some implementations, a cutout is provided wherein the cutout allows for fluid communication, such as from an interior to an exterior of a bearing. For example, where a shaft is provided, the shaft may include a cutout where the cutout is configured for allowing fluid communication between proximal and distal portions of the shaft, such as proximal to one or more bearings. In other implementations, such as where the shaft is configured for driving the piston in an orbital motion, the shaft may include a generally cylindrical eccentric member that is offset from a centerline of the shaft. The eccentric member may include one or more bearings and therefore may be configured to include one or more cutout portions for allowing fluid communication between axial ends of the eccentric member, e.g., proximal to one or more of the bearings.

In some implementations, the dual cylinder rotary piston compressor of the disclosure does not have a fluid lubricant other than the process fluid within contact of either of the chambers. Further, each chamber may be in fluid communication with a pressure source.

The subject matter described herein provides many advantages. For example, the rotary systems described herein can use only the fluid being processed (for example, compressed or vacuumed) for lubrication while not requiring any another lubricant for lubrication. The absence of another lubricant prevents a likely contamination of the fluid to be processed by such a lubricant. Moreover, the rotary systems described herein more fuel-efficient than conventional compressors or vacuum pumps. Further, the rotary systems produce minimal or no noise, thereby being significantly quieter than their traditional counterparts. Furthermore, the rotary systems described herein use less power than conventional compressors or vacuum pumps, and have a longer life than such conventional counterparts. Moreover, the rotary systems described herein vibrate less than the traditional compressors or vacuum pumps. The rotary systems are useful for various medical applications and other clean gas applications, especially those where conventional lubricants can contaminate the fluid being processed.

Other and further aspects, objects, features, and advantages of the present disclosure will become better understood with the following detailed description of the accompanying drawings.

BRIEF DESCRIPTION OF THE DRAWINGS

FIG. 4b shows a partial front elevated view similar to FIG. 4a, and shows the vane chamber and the suction chamber no longer in fluid communication.

FIG. 5 shows a front elevated view of a piston with a vane and shows concentric outside diameter and inside diameters.

FIG. 23a shows a cross-sectional view showing two rotary compressors operated by a single motor.

FIG. 25a shows a cross-sectional perspective view of a rotary compressor showing geometries for equalizing pressures across a sealed bearing.

FIG. 25b shows geometry for venting a shaft bearing when mounted in an endplate.

FIG. 25c shows a magnified view of a portion of the system shown in FIG. 25a.

DETAILED DESCRIPTION

FIGS. 1-25c describe various implementations of rotary systems. Each rotary system can be either a rotary compressor or a rotary vacuum pump. The rotary system can include a corresponding piston that rotates in an orbital motion around a respective eccentric of a shaft in order to either compress fluid or function as a vacuum pump. In some implementations, multiple rotary systems can be executed in parallel on a single shaft such that these rotary systems are powered by a single motor.

Figure 1:
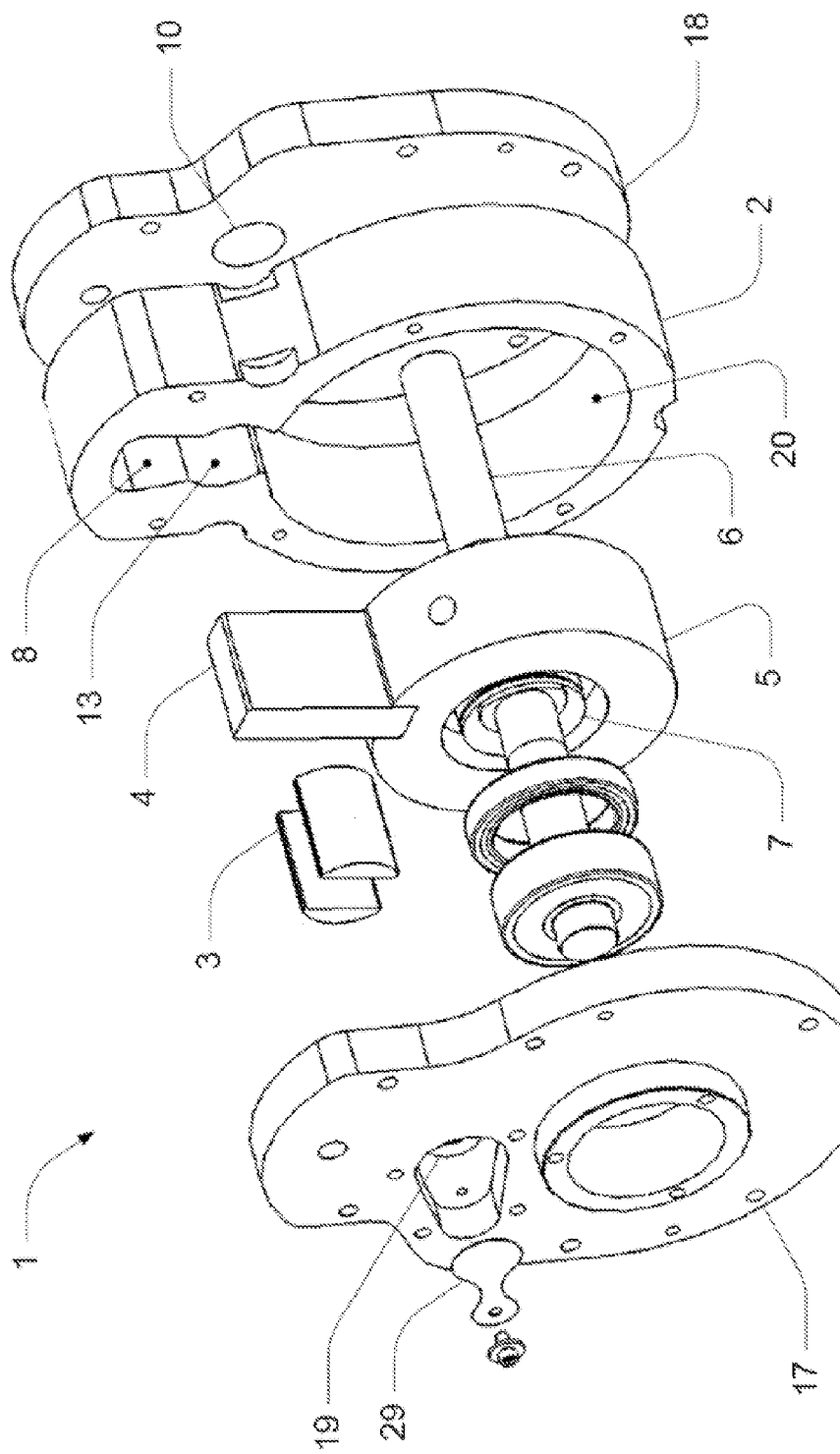
FIG. 1 shows an exploded perspective view of an implementation of a rotary compressor.

FIG. 1 shows an exploded view of a rotary compressor 1. An exemplary rotary compressor 1 of the disclosure includes several inter-related parts.

The compressor can include a housing, which may be formed as a stator 2 and can include two endplates, which are a discharge endplate 17 and a suction endplate 18. The discharge endplate 17 can include a discharge port 19, and the suction endplate 18 can include a suction port 10. In alternate implementations, both the discharge port 19 and the suction port 10 can be implemented on a single endplate, which can be either of discharge endplate 17 and suction endplate 18. In another implementation, the discharge port 19 and the suction port 10 can be implemented on the stator 2. In yet another implementation, the discharge port 19 and the suction port 10 can be implemented on one or more parts of the compressor housing. Further, although the discharge endplate 17 and the suction endplate 18 endplates are shown as being separate from the housing, in some implementations, the discharge endplate 17 and the suction endplate 18 can be an integral part of the housing such that these endplates 17 and 18 are machined together with the housing.

The stator 2 includes an outer perimeter surrounding a cavity, which includes a vane chamber 8, a bushing chamber 13, and a cylindrical bore chamber 20. The vane chamber 8 can reside a vane 4. The bushing chamber 13 can reside bushings 3. The bore chamber 20 can reside the piston 5, which can move in an orbital fashion around a shaft 6 in order to form a suction volume and/or a compression volume.

Although the stator 2 is shown to enclose a vane chamber 8, a bushing chamber 13, and a cylindrical bore chamber 20, in other implementations, the stator 2 can have different configurations. For example, the vane chamber 8 and the bushing chamber 13 can form a single chamber. The stator 2 can include opposing axial surfaces, such as a front surface configured to be attached to the discharge endplate 17 and a back surface configured to be attached to the suction endplate 18, in order to enclose the collective space of the vane chamber 8, the bushing chamber 13, and the cylindrical bore chamber 20.

The vane 4 can have a first portion and a second portion. The first portion of the vane 4 can be associated with the piston 5. The second portion of the vane 4 can extends into one or both of the bushing chamber 13 and vane chamber 8. In some implementations, the vane 4 can be firmly attached to the piston 5 such that there is no movement between the vane 4 and the piston 5. Such a firm attachment can occur during the original machining of these components, or subsequently by gluing, soldering, screwing by screws, pinning by pins, and/or any combination thereof. In other implementations, the vane 4 can be detachably attached to the piston 5. For example, the vane 4 can be temporarily fitted into a cut in the piston 5.

The bushing chamber 13 can allow one or more bushings 3 and the vane 4 to reside. Although two bushings 3 are shown, in alternate implementations, one or more than two bushings may be implemented. The flat surfaces of the vane 4 can form a movable seal (for example, a fluid seal) with the flat surfaces of the bushings 3. In other implementations, the bushings 3 can be of any shape and design as long as they are capable of mating with the vane 4 to form a movable seal. In one implementation, one or more of the bushings may have a different shape or size. For example, the bushing may include a first curved surface disposed in a bushing chamber and a second curved surface contacting the vane 4. The first curved surface can have a radius smaller than the radius of the second curved surface. In further implementations, surface of one or more of the bushings 3 can additionally include one or more dimples. In some implementations, one or more of the bushings 3 can be formed of multiple parts in an axial direction, wherein use of some parts can be optional such that a user can vary the overall axial length of the bushings 3.

Additionally, one or more bushing bearings may be present within the bushing chamber 13. Alternately, the bushing chamber 13 may be configured to form a bushing bearing. The bushing bearing(s) may be affixed to the bushing chamber 13. One or more additional elements, such as a compliant member, as described below, may further be present within the bushing chamber 13 and/or associated with a bushing bearing and/or bushing 3. In some implementations, at least one of the vane 4 and the bushing bearing may have one or more abradable coatings. The vane 4 and the bushing bearing can have different abradable coatings. For example, the vane 4 can have a relatively soft coating, and the bushing bearing can have a relatively hard coating. The abradable coating can have a polymer base or a metal base, such as a nickel base.

The bushing chamber 13 of the stator 2 can be formed by opposing curved surfaces interfacing with bushing bearings, which in turn interface with bushings 3. Accordingly, the bushings 3 can include both: (i) a curved surface designed to fit snugly within the curved recess of the bushing chamber 13 and/or bushing bearings positioned in the bushing chamber 13, and (ii) a relatively flat surface designed to interface with a flat surface of the vane 4. The bushings 3 in conjunction with the vane 4 can form a movable seal (for example, a fluid seal) that separates the suction space and the compression space of the bore chamber 20 from the vane chamber 8.

The piston 5 is a cylindrical member having an exterior radial surface, an interior radial surface, a first axial surface, and a second axial surface. This diameter of the exterior radial surface of the piston 5 is less than the diameter the cylindrical bore chamber 20 such that the piston 5 can move within the cylindrical chamber 20 in an orbital motion around the shaft 6. The interior radial surface of the piston 5 forms an orifice, within which the shaft 6 and a shaft eccentric 7 are positioned. The exterior portion of the piston 5 includes a cut out portion (for example, a vane cleft), which can receive a distal portion (that is, the lower portion, as shown) of the vane 4. The vane 4 is affixed to the piston 5 such that relative motion between the vane 4 and piston 5 does not occur. Alternatively, the vane 4 and piston 5 can be a single machined component. The vane 4 interacts with the piston 5 and the bushings 3 so as to form a compression chamber 14 and a suction chamber 15 within the bore chamber 20.

The piston 5 can move in an orbital motion within the bore chamber 20. The shaft 6 and the shaft eccentric 7 function together to cause the piston 5 to orbit within the bore chamber 20. The shaft 6 can be elongated and cylindrical in shape. The shaft 6 can pass through, via bearings, the endplates 17 and 18 and/or corresponding bores therein. In alternate implementations, the shaft 6 can be otherwise associated with the endplates 17 and 18. The shaft 6 can be further configured for rotating. The shaft eccentric 7 can interface with the shaft 6 and the piston 5 via associated bearings, such as rolling element bearings that are a part of the shaft eccentric 7. The rolling element bearings can include a needle and a ball bearing. The shaft eccentric 7 is configured for interacting with the piston 5 via a rolling element bearing such that the centerline of the piston 5 is offset from the centerline of the bore chamber 20. This offset movement of the piston 5 enables the orbital motion of the piston 5 in the bore chamber 20. In some implementations, as the piston 5 moves, the compression chamber 14 and the suction chamber 15 (described below) do not overlap the roller element bearings, which are fitted within elements of the piston 5 and the shaft eccentric 7. Also, the shaft 6 and shaft eccentric 7 describe one way of affecting the orbital motion of the piston 5. According to another way, the piston 5 can contain permanent magnets such that a motor coil not contacting the piston 5 can drive the piston 5 in an orbital motion.

As the piston 5 orbits within the bore chamber 20, the vane 4 moves up and down against the bushings 3 within the vane chamber 8. Therefore, the flat surfaces of the vane slide up and down against the flat surfaces of the bushings 3. This contact interface functions to form a bearing and a seal separating the vane chamber 8 from the bore chamber 20. The configuration and motion of the piston 5 with respect to the vane 4 divides the bore chamber 20 into two separate chambers (that is, a suction chamber 15 and a compression chamber 14, as described below).

The vane 4 in conjunction with the piston 5 separates some of the volume of the bore chamber 20 into two a suction volume (of the suction chamber 15) and a compression volume (of the compression chamber 14). Additionally, the bushings 3 interact with the vane 4 to separate this compression volume and the suction volume from the volume within the vane chamber 8.

As shown, the piston 5 is offset from a radial center of the bore chamber 20 when the piston 5 performs the orbital motion. As the piston 5 orbits within the bore chamber 20, the outer radial surface of the piston 5 can form contact with the surface of the stator 2 with there being a small radial clearance between the outer radial surface of the piston 5 and the surface of the stator 2. This small radial clearance may be from about 1 micron up to and about 50 microns (including 50 microns). In an alternate implementation, the radial clearance may range from about 1 micron to about 100 microns. In yet another implementation, the radial clearance may range from about 20 microns to about 80 microns. In one implementation, the radial clearance may range from about 40 microns to about 60 microns. In another implementation, the radial clearance may be about 50 microns. Additionally, there can be axial clearance between axial surfaces, such as between the piston 5 and endplates 17 and 18. In different implementations, this axial clearance can have the following values: (a) values ranging from about 1 to about 100 microns, (b) values ranging from about 20 to about 80 microns, (c) values ranging from about 40 to about 60 microns, or (c) about 50 microns. In certain implementations, a compression ratio between an absolute pressure of discharge of the compressor and an absolute pressure of suction of the compressor can be one of the following: (a) between about 1 and about 5, (b) between about 2 or 2.5 and 4, or (c) between about 3 and about 3.15.

Further, as shown, the endplate 18 includes a suction port 10. The suction port 18 is coincident with a portion of the bore chamber 20 such that a fluid (for example, a gas) may be passed into the bore chamber 20 in order to fill the vacant space in the bore chamber 20 and form a suction volume (of the suction chamber 15). As the piston 5 orbits within the bore chamber 20, the piston 5 increasingly covers over the suction port 10, thereby converting the suction volume into a compression volume (of the compression chamber 14).

Additionally, as shown, the discharge endplate 17 includes a discharge port 19. The discharge port 19 is connected to a portion of the bore chamber 20 such that a compressed gas may be passed through the discharge port 19, thereby evacuating the bore chamber 20. Accordingly, as the piston 5 orbits within the bore chamber 20, a suction volume of a fluid is generated, the fluid is compressed while creating a compression volume of the fluid, and the fluid is discharged through the discharge port 19 of the endplate 17. The movement of the piston 5 within the bore chamber 20 is described in greater detail below with reference to FIG. 2. Other components of the compressor such as fasteners are not shown in FIG. 1.

The liquid being processed (for example, compressed) by the rotary compressor 1 lubricates the compressor. The fluid that is to be processed can be ambient air, which can include at least: oxygen, nitrogen, and argon. In alternate implementations, the fluid that is to be processed can be any other fluid, such as at least one liquid or at least one gas. The use of the liquid being processed for lubrication along with specific structural details (for example, abradable coating and/or other details described below) prevent a need of a fluid lubricant (for example, a liquid lubricant or non-Newtonian fluid, such as pseudoplastic, a dilatant, a Bingham plastic, a thixotropic, a rheopectic, and a viscoelastic, and/or any other non-Newtonian liquid) specifically for performing lubrication of the rotary compressor. The abradable coating on the surfaces of the piston 5, the vane 4, and/or the endplates 17 and 18 prevents (or minimizes, in some implementations) friction caused by touching of these components with surfaces of other components of the rotary compressor 1, thereby eliminating the need for a separate lubricant besides the fluid that is being processed. Therefore, such a separate lubricant is not present within one or more of: the vane chamber 8, the bushing chamber 13, and the bore chamber 20, which includes the suction chamber 15 or the compression chamber 14. In some alternate implementations, a separate lubricant can be used only if this lubricant is completely encased and sealed within an element (for example, within one or more bearings, such as a shaft bearing or an eccentric bearing) of the rotary compressor 1.

A radial clearance between external radial surface of the piston 5 and surface of the bore chamber 20 can be equal to or less than about 50 microns. A radial clearance between axial surfaces of the piston 5 and the endplates 17 and 18 can be equal to or less than about 50 microns. The compression ratio between a pressure of discharge volume of the fluid and a pressure of suction volume of the fluid may be within the range of between about 1 and about 2.5. Further, the rotary compressor 1 operates as a part of a system that does not re-circulate a closed volume of fluid, which is to be compressed, repeatedly.

Figure 2:
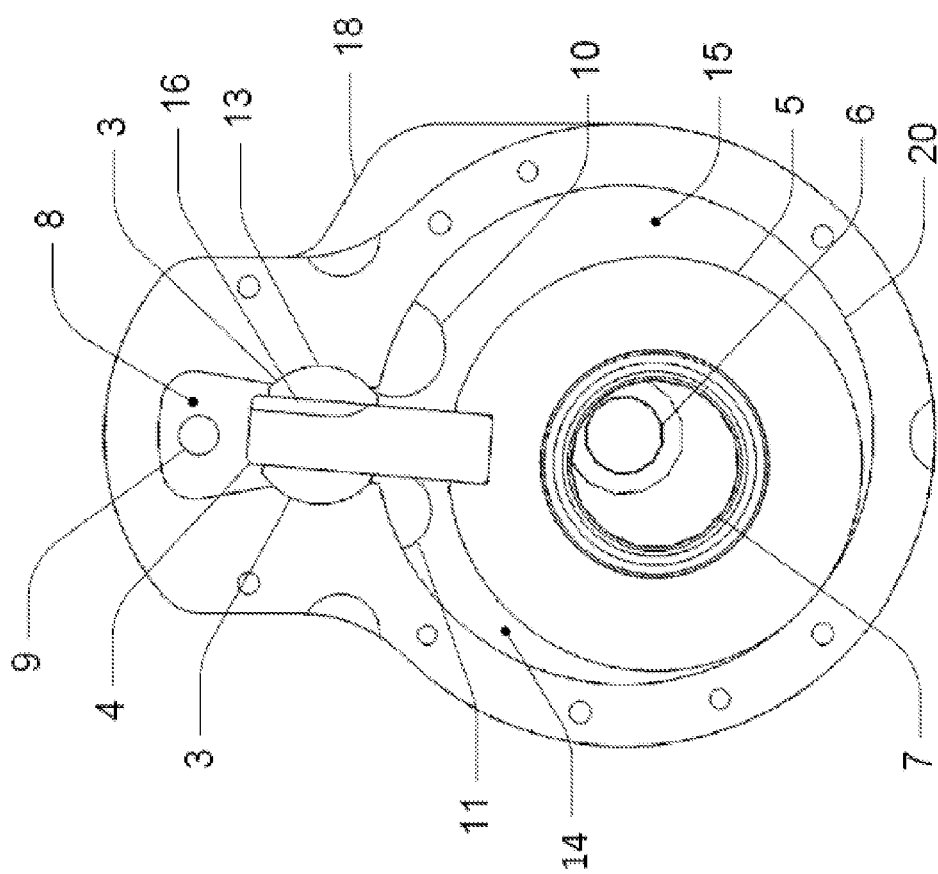
FIG. 2 shows a front elevated view of an implementation of a rotary compressor.

FIG. 2 shows a front view of the rotary compressor 1. The inlet or suction port 10 is visible in the suction endplate 18. The discharge endplate 17 is removed in this view for clarity. The location of the discharge port (not shown) is evidenced by the discharge dimple 11 that is located in the suction endplate 18. In an alternate implementation, the suction endplate 18 or the discharge endplate 17 may be integral with the stator 2. In yet another implementation, the suction port 10 and/or discharge port 19 can be positioned on the housing, as shown at least by FIG. 23 described herein.

The shaft 6 has a cylindrical shaft eccentric 7, the centerline of which is parallel to but not concentric with the shaft 6 centerline. The shaft eccentric 7 occupies the space enclosed by the inner radial surface of the piston 5, and is rotatably mounted with the inner radial surface of the piston 5 such that the centerline of the piston 5 is eccentric with respect to the centerline of the stator bore chamber 20. The interface between the shaft eccentric 7 and the inner surface of the piston 5 may additionally include one or more bearings, such as rolling element bearings, plain bearings, journal bearings, and the like.

As the shaft 6 rotates (for example, clockwise), the offset shaft eccentric 7 rotates, thereby driving the piston 5 around in a rotation that is approximately orbital. The eccentricity of the piston 5 is such that outer radial surface of the piston 5 contacts or nearly contacts a small zone of the surface of the stator 2. The vane 4 extends radially from the piston 5. The vane is slidably engaged between the two bushings 3. The bushings 3 are rotatably engaged in the in the bushing chamber 13.

As the shaft 6 continues to rotate, the piston 5 is driven along a circular or orbital path. Rotation of the piston 5 is limited by the engagement of the vane 4 with the bushings 3. Therefore, the motion of the piston 5 is nearly orbital.

The arrangement of the vane 4 and the eccentricity of the piston 5 are such that the volume within the bore chamber 20 is divided into a suction chamber 15 and a compression chamber 14. As the shaft 6 rotates (for example, clockwise) with respect to FIG. 2, fluid that is to be processed is passed (via tubing connected to a fluid source) through the inlet port 10, and into the suction chamber 15. The volume of the suction chamber 15 increases while the volume of the compression chamber 14 decreases. This increasing volume of the suction chamber 15 causes fluid to be drawn into the suction chamber 15 via the suction port 10. As the piston 5 moves in its orbital rotation, the suction port 10 gets increasingly closed off by the piston 5 and the suction volume becomes a compression volume. As the piston 5 continues in its rotation, the compression volume decreases. The decreasing volume of the compression chamber 14 compresses the fluid in the compression chamber 14 until the pressure in the compression chamber is approximately the same pressure as the fluid downstream of the discharge port 19.

A valve may be present covering the downstream end of the discharge port 19 in a manner that the general flow of fluid is only permitted out of the compression chamber 14. For example, when the pressure within the compression chamber is about equal to or greater than the pressure downstream of the discharge valve 29, the valve is caused to open and the fluid is forced out of the compression chamber 14.

As the shaft 6 continues to rotate, the volume of the compression chamber 14 reaches a minimum and the volume in the suction chamber 15 reaches a maximum. Additional rotation isolates the suction volume 15 from the suction port 10. At this point the suction chamber 15 becomes the compression chamber 14. This cycle repeats as the shaft 6 rotates, such that a continuous flow of compressed fluid is produced. Hence, fluid is continuously drawn in on one side, compressed and discharged on the other side of the larger bore chamber 20 of the rotary compressor 1.

A vane chamber 8 is located near the top of the compressor in the FIG. 2 orientation. The vane chamber 8 acts in part as a clearance for the vane 4 such that as the piston 5 rotates, the vane 4 is moved up and down in and out of the vane chamber 8 in a linear and/or rotational oscillation. An optional vane chamber vent 9 is located in the vane chamber 8. The vane chamber vent 9 may be included so as to control the fluid pressure within the vane chamber 8. The vent 9 may be controlled by an external or internal source. For example, in some implementations, a pressure source may be provided wherein the pressure source is in fluid communication with the vane chamber portion, e.g., through a controlled vane. Accordingly, a control mechanism may also be provided so as to control the fluid pressure in the vane chamber 8. In some implementations, the control mechanism may control one or more of the valve and/or a pressure source. The pressure source may be any suitable pressure source, and in some implementations, the pressure source may include an ambient pressure source, a pressure source that is above ambient pressure, or a pressure source is below ambient pressure.

In one implementation, an improved mechanism for controlling the load and wear on the contacting surfaces of the vane 4 and/or bushings 3 is provided. The vane chamber 8 is located in the stator 2. During a portion of the shaft 6 rotation, the vane extends into the vane chamber 8. In general, the vane chamber 8 is not in fluid communication with the suction chamber 15 or the compression chamber 14. Therefore, in addition to moments and forces imparted by the kinematics of the device, three distinct fluid pressures act on the vane 4 and bushings 3. These pressures can act on the bushings 3 and vane 4 in a way that increases friction. This is detrimental to the performance and reliability of the rotary compressor 1.

The fluid pressure in the vane chamber 8 is advantageously controlled, as maintaining a constant pressure in this vane chamber can be disadvantageous, as noted below. For example, when the piston 5 is nearest the bushings 3 the pressure in the compression chamber 14 may approximately be equal to the pressure in the suction chamber 15. If pressure in the vane chamber 8 is at the discharge pressure, fluid (for example, gas) can leak around the vane 4 and bushings 3 into the compression chamber 14 and/or suction chamber 15. This can result in a loss of efficiency.

In addition, there is pressure loading on the vane 4 and bushings 3 which can result in increased friction and wear. For example, if the vane chamber 8 is in fluid communication with the suction chamber 15 then pressure on the vane 4 is initially balanced. However, as the shaft 6 rotates and the fluid is compressed a pressure load may be induced on the compression chamber side bushing 3. This fluid pressure imbalance can lead to leakage from the compression chamber 14 to the vane chamber 8. This would also result in a loss of efficiency. Furthermore, the same fluid pressure imbalance imparts a force on the compression chamber side bushing 3 that urge the bushing into the vane chamber 8. This can increase friction between the vane 4 and bushings 3 and between the bushing chamber 13 and bushings 3. This would also result in a loss of efficiency.

Figure 22:
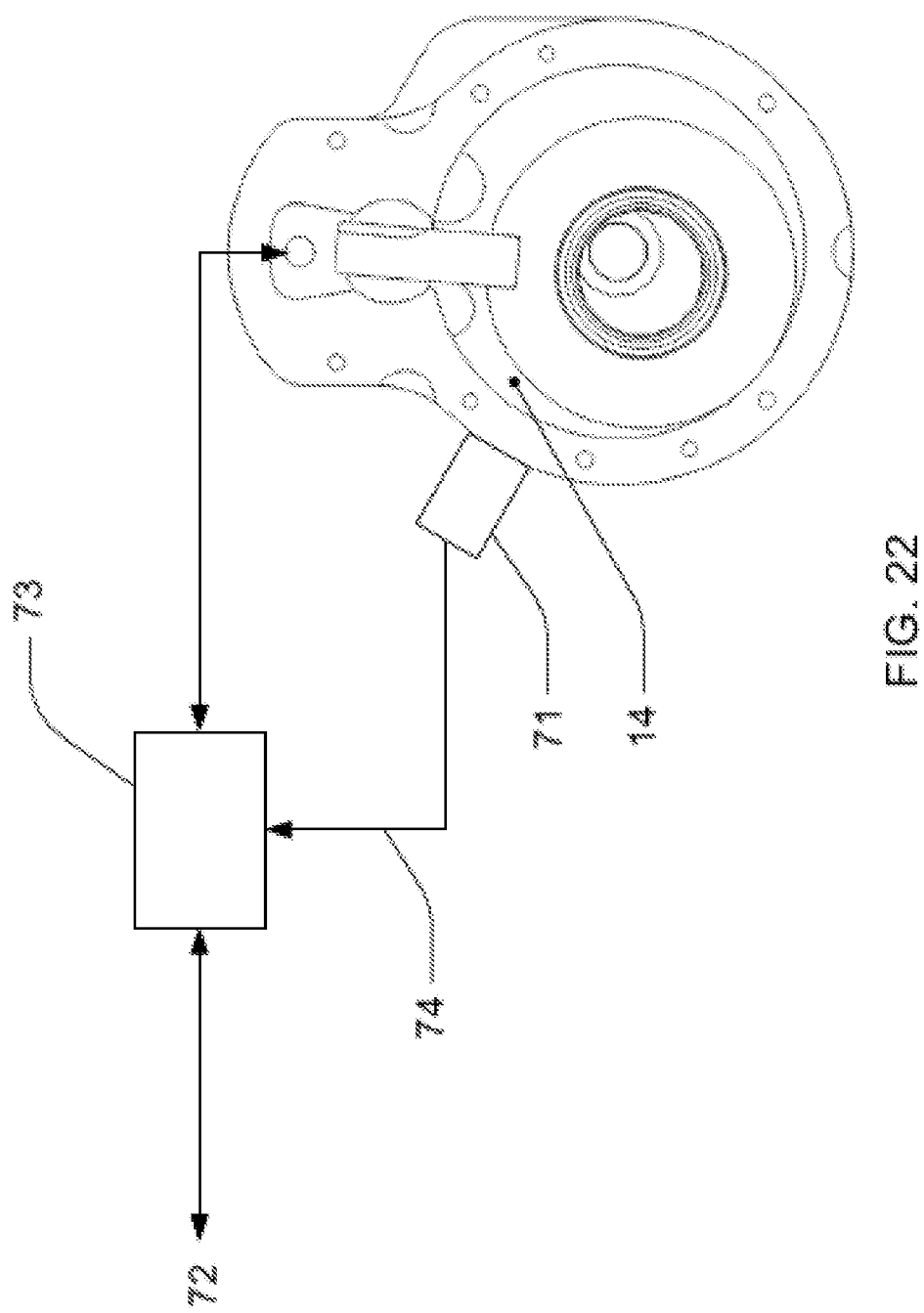
FIG. 22 shows a front elevated view, similar to FIG. 19, and shows a rotary compressor system and associated control system.

In one implementation, therefore, the vane chamber 8 is sealed so that it is not in fluid communication with any other fluid volume. In some practical devices some fluid leakage paths may be unavoidable, but these are insignificant with respect to the present implementations. With the vane chamber 8 sealed, this volume can be purposefully set to a fluid pressure that is independent of the fluid pressure in the suction chamber 15, compression chamber 14, and/or discharge volume downstream of the discharge valve 29. This pressure can be held constant or be allowed to vary in time via a control mechanism as shown in FIG. 22, described in greater detail herein below. In this way the pressure in the vane chamber 8 can be optimized to minimize wear and leakage of the fluid being compressed.

Accordingly, another object of the present disclosure is to provide a control mechanism for controlling the pressure in the vane chamber 8. In one implementation, the vane chamber 8 volume is fixed, except that the motion of the vane 4 into and out of the vane chamber 8 compresses and expands a fluid, e.g., a gas, therein as the vane enters and leaves the vane chamber 8. More specifically, when the piston 5 is furthest from the vane chamber 8 the vane 4 protrudes into the vane chamber 8 minimally. In this position, the vane chamber 8 is at its maximum fluid volume. However, when the piston 5 is closest to the vane chamber 8, the vane 4 protrudes into the vane chamber 8 a maximum amount. Therefore, at such a position, the vane chamber volume is at a minimum. The vane chamber volume, therefore, varies between the maximum and minimum values nearly sinusoidally (that is, in a sinusoidal manner) as the shaft 6 rotates. Therefore, the gas entrapped in the vane chamber 8 alternately becomes compressed and expanded with a corresponding rise and fall in pressure. In so doing, the vane chamber pressure can be used to minimize leakage of the fluid being compressed, and minimize wear of the vane 4 and bushings 3 without the need for external control means.

Figure 3:
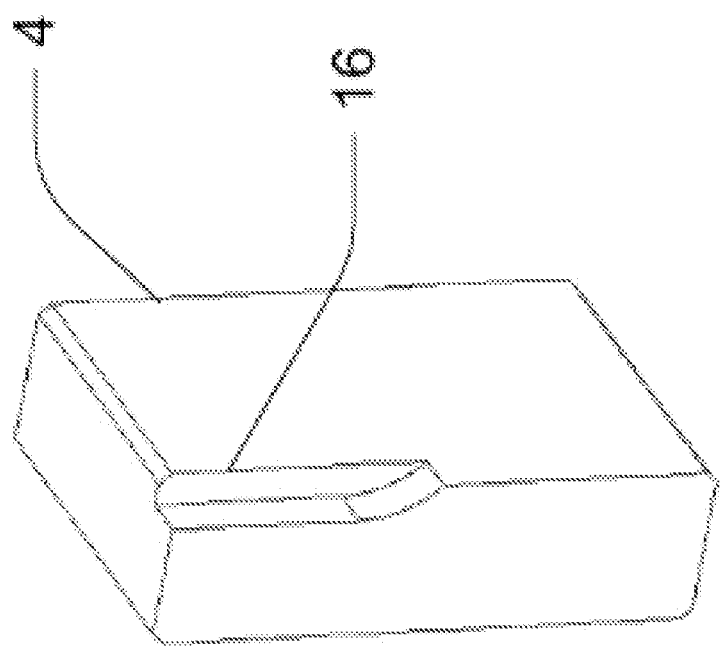
FIG. 3 shows a perspective view of an implementation of a vane of the rotary compressor of FIG. 2.

Another object of the present disclosure is a mechanism for controlling the vane chamber 8 pressure (that is, pressure within the vane chamber 8) that is independent of the vane 4 position within the chamber for a certain portion of the crank revolution. For example, in one implementation, a relief 16 is cut into a portion of the vane 4 as shown in FIGS. 2 and 3. The relief 16 is shown on the suction chamber 15 side of the vane 4. The length of the relief 16 is such that when the vane 4 protrudes minimally into the vane chamber 8, e.g., the piston 5 is furthest away from the vane chamber 8 and bushings 3, there is fluid communication between the vane chamber 8 and the suction chamber 15. When this occurs, the fluid pressure in the vane chamber 8 and suction chamber 15 equalizes. This occurs when the piston 5 is relatively far from the vane chamber 8 and bushings 3. As the shaft 6 continues to rotate and the piston 5 approaches the vane chamber 8 and bushings 3, the vane 4 is pushed further into the vane chamber 8. As the piston 5 moves closer to the vane chamber 8 and the bushings 3, the surface of the bushing 3 covers the vane relief 16. Continued shaft rotation causes the vane to protrude into the vane chamber 8, which increases the pressure in the vane chamber.

In this way, the pressure in the vane chamber 8 varies with crank angle and the load the pressure in the vane chamber transmits to the bushings 3 may be controlled.

For example, the pressure can be varied, e.g., to be about equal to the pressures in the suction and/or compression chambers. This may be important in situations where the pressure in the suction chamber 15 is lower than the pressure in the vane chamber 8 and such pressure differential results in a frictional force being applied to the bushing 3, which force tends to push the bushing, or a portion thereof, into the vane chamber 8. Having vane relief or cutout 16 in vane 4 equalizes the two pressures, e.g., when the piston 5 is furthest away from the bushings, thereby negating this disruptive force and minimizing wear on the bushing 3.

As the piston 5 continues in its rotation and the compression pressure in the compression chamber increases, the cutout moves upwards and is covered by the bushing 3, thereby resulting in an equivalent increase of pressure in the vane chamber 8. Hence, the pressure in the compression chamber 14 also varies with crank angle. Therefore, using this approach the pressure imbalance on the left bushing 3 can be minimized. Accordingly, this reduces friction and wear of the bushing. The length of the vane relief 16 can be varied to optimize the position of the piston 5 at which fluid communication between the vane chamber 8 and suction chamber 15 begins and ends. Furthermore, the volume of the vane chamber 8 and the geometry of the vane 4 can be varied to optimize the change in vane chamber pressure with position of the piston 5.

Figure 4A:
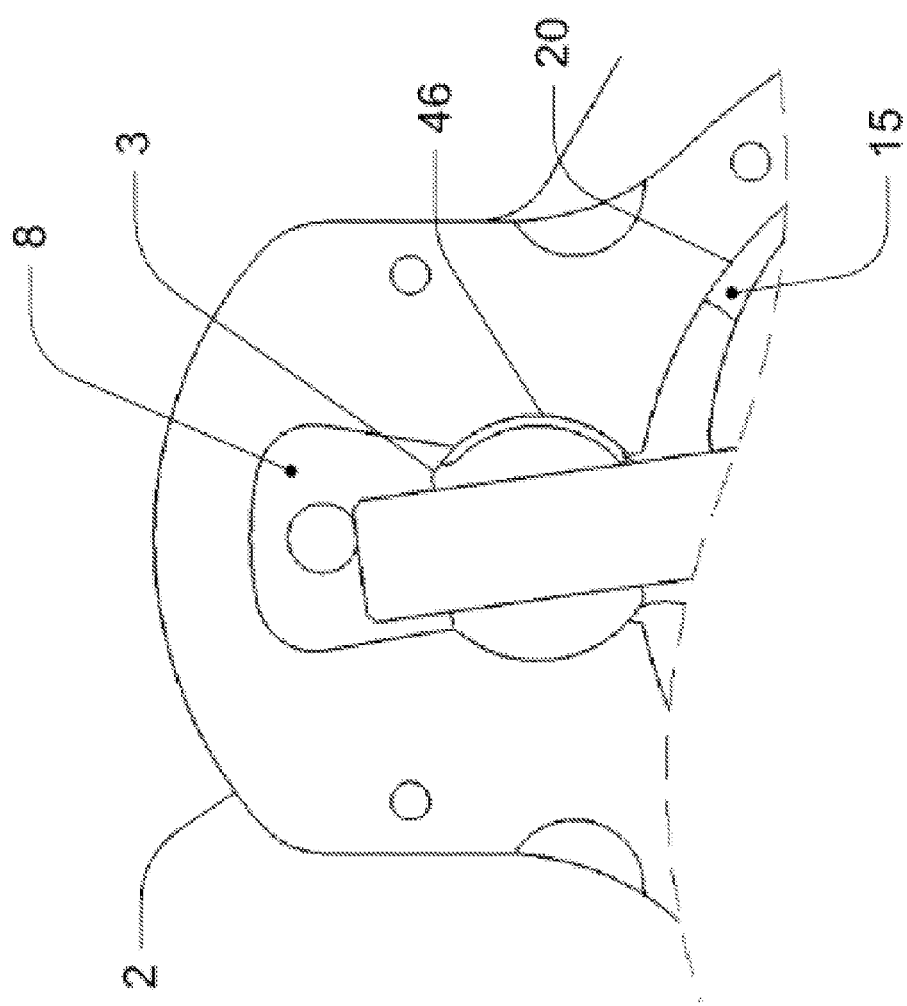
FIG. 4a shows a partial front elevated view of an implementation of a stator and bushing with a chamfer added to the bushing on a suction chamber side, and shows a vane chamber and a suction chamber in fluid communication.
Figure 6:
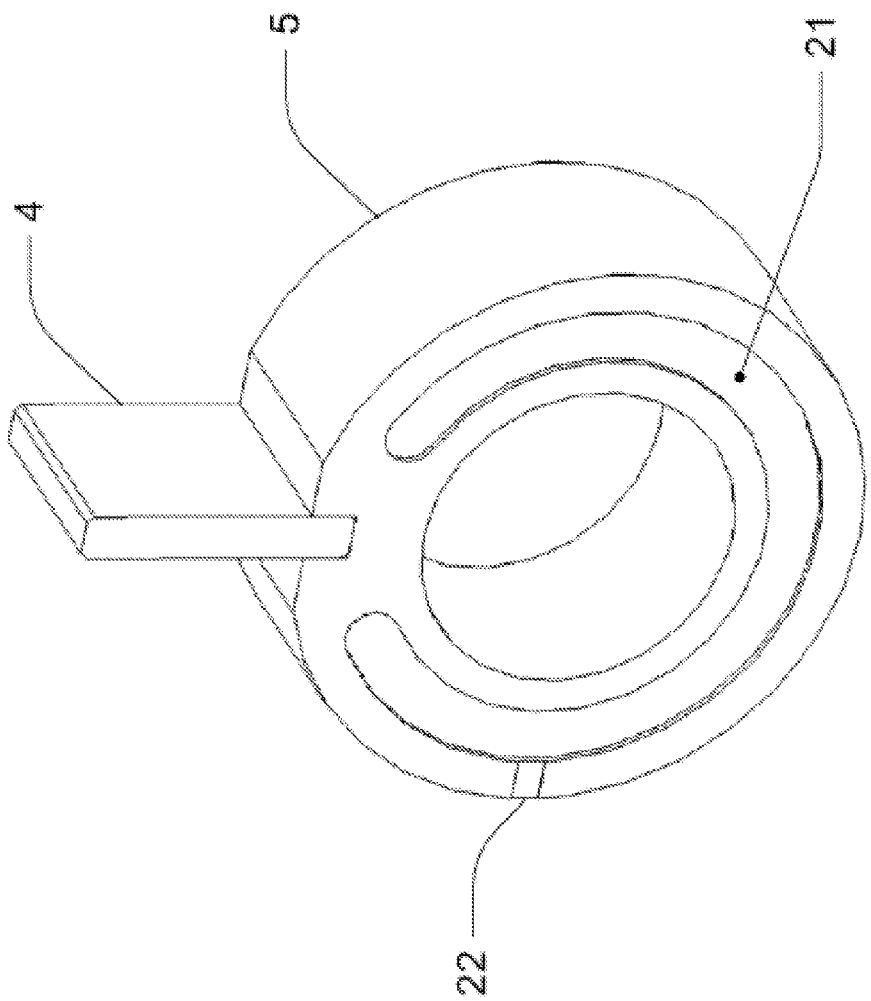
FIG. 6 shows a perspective view of an implementation of a piston and shows piston recesses formed in axial faces of the piston.

FIG. 4 shows an implementation that is similar to the FIG. 3 implementation for controlling pressure within the vane chamber. In this implementation a relief cut or chamfer 46 is added to the bushing 3 at the bushing chamber/bushing bearing surface interface of the stator 2. The relief cut is positioned on the bushing on the suction chamber 15 side of the large bore chamber 20. The length of the chamfer is such that at certain positions of the orbit of the piston 5, the vane chamber 8 and suction chamber 15 are in fluid communication, as depicted in FIG. 4 (*a*); whereas at other crank angles, the chambers are no longer in fluid communication, as depicted in FIG. 4 (*b*). Other configurations are possible and would be obvious to one with ordinary skill in the art.

Other problems can also affect the efficiency of fluid compression as well as increase wear on the components of the rotary compressor. For example, as described with reference to FIG. 2, when the discharge port is located in one of the endplates of the rotary compressor, e.g., discharge endplate 17, the piston 5 in its orbital movement covers the discharge port for part of the crankshaft revolution. When this occurs, the axial face of the piston 5 may be exposed to discharge pressure. This may result in an axial force being exerted on the piston 5, which in turn can causes the piston 5 to move axially, thereby contacting the opposing endplate, e.g., suction endplate 18. This contact can result in excessive wear or damage to the suction endplate 18 and/or the piston 5. This is especially true for oil-less compressor designs because there is no lubricant present to prevent contact between said components. A similar effect is possible when the suction port is located in the suction endplate 18. The suction endplate 18 and discharge endplate 17 are collectively referred to herein as endplates.

Figure 2A:
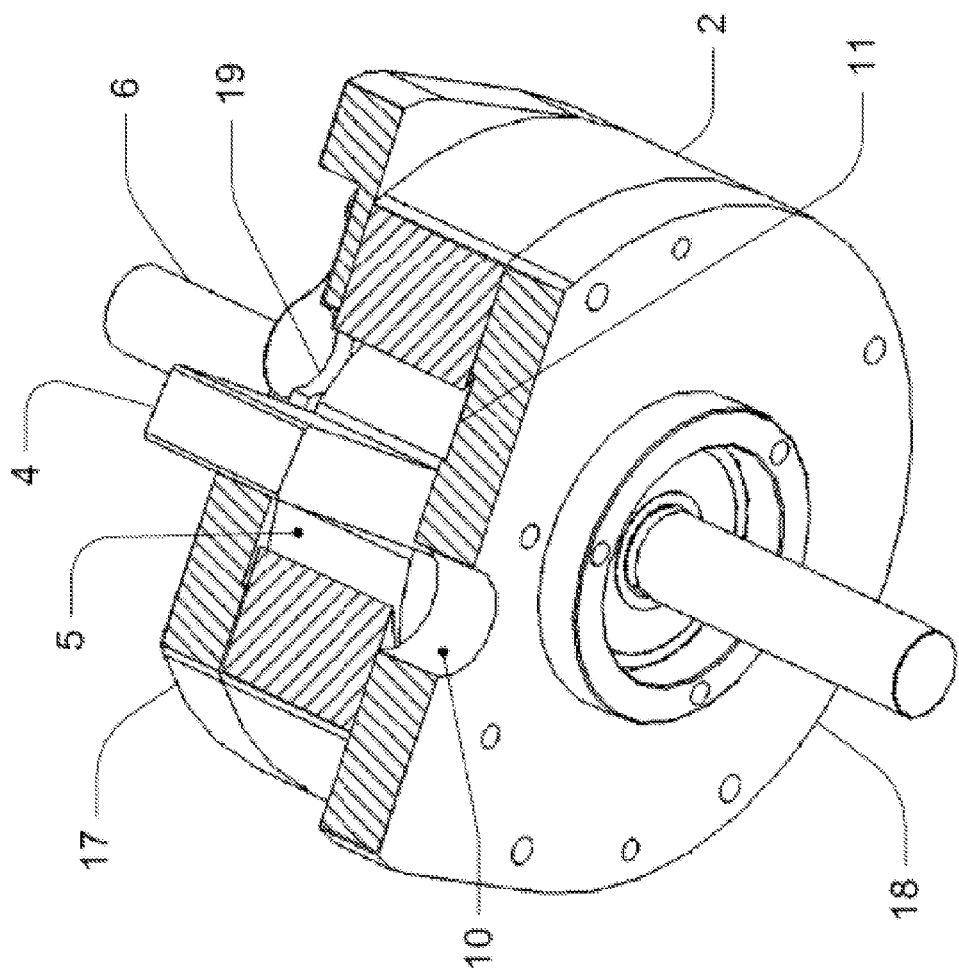
FIG. 2a shows a perspective cross-sectional view of an implementation of a rotary compressor.

Accordingly, in one implementation, a recess is formed in the opposing endplate. The recess may be positioned radially and circumferentially so that it is in approximate alignment with the discharge port 19 and/or the suction port 10. Specifically, the suction endplate 18 may have a discharge dimple 11 (see FIG. 2*a*) and the discharge endplate 17 may have a suction dimple (see FIG. 2*a*). The discharge dimple 11, compression chamber 14, and volume upstream of the discharge port valve are all in fluid communication at least until the piston 5 fully covers the discharge port 19 and discharge dimple 11. The discharge port 19 and discharge dimple 11 may remain in fluid communication even when the piston 5 fully covers the discharge port 19, due to natural flow paths in the area of the vane 4 and bushings 3 and the proximity of the discharge port 19 to the vane 4. For example, in certain implementations, the rotary compressor includes a discharge port that is positioned in one endplate wherein the second endplate includes a cutout portion that forms a blind hole which is in axial opposition to the discharge port.

The pressure of gas in the discharge dimple 11 is similar to the pressure of gas upstream of the valve in the discharge port 19. Therefore, an axial force imposed on the piston 5 by gas pressure in the discharge port is balanced by the axial force imposed on the piston 5 by gas pressure in the recess. The shape and size of the recess are similar to that of the discharge port, although other shapes and sizes could be devised that would have similar effect. The suction dimple has a similar effect. Other forces can also cause the piston 5 or vane 4 to come into contact with one of the endplates. For example, if the shaft 6 is parallel with gravitational acceleration, the piston 5 tends to be pulled into contact with one of the endplates.

In another implementation, arbitrary axial forces can prevent contact between the piston 5 and endplates 17 and 18. In this implementation, shown in FIG. 6, piston recesses or reliefs 21 are formed in one or both of the axial faces of the piston 5 so as to create a hydrostatic bearing between the surfaces of the opposing surfaces of the piston 5 and the endplates. These recesses may be in fluid communication with fluid (for example, gas) in the compression chamber for a portion of the crank revolution. For example, such communication can occur with a flow path 22 between the large bore chamber, e.g., compression chamber 14, and piston recess 21, so as to pressurize the space between the recess and the endplate. It can also occur when the piston recess 21 and discharge port 19, or discharge dimple 11, intersect for a portion of rotation of the shaft 6. Such fluid communication pressurizes the piston recesses 21 to a pressure similar to that of the compression chamber 14. It is understood that once the piston recess 21 is pressurized some of the pressurized fluid may leak out of the recess because there may be a very small but non-zero clearance between the axial face of the piston 5 and the endplates.

If an axial force causes the piston 5 to move toward one endplate, e.g., the suction endplate 18, the leakage clearance between the suction endplate 18 and axial face of the piston 5 decreases. This reduces the leakage rate of fluid from the piston recess 21 on the side of the suction endplate 18. The leakage of fluid from the piston recess 21 on the side of the discharge endplate 17, however, increases. This results in a pressure imbalance, which pushes the piston 5 axially away from the suction endplate 18, thus preventing contact between these components. This restoring force works in both directions along the axial axis such that the piston 5 floats between the endplates without contacting them.

The general shape of the compressor piston 5 is that of a right circular cylinder with a vane 4 portion extending radially from the piston 5 outside diameter. A generally cylindrical hole is situated concentrically with the piston 5 outside diameter. This hole accepts a drive means which drives the piston 5 eccentrically with respect to the center line of the stator bore 20.

FIG. 5 shows a vaned piston 23, which is a combination of the piston 5 and the vane 4. In this configuration the piston 5 outside diameter and inside diameter are concentric. The center of mass of the piston 5 with a vane 4, therefore, is not at the horizontal center line of the inside diameter. This causes an imbalance when the compressor is running that is not easily corrected with simple counterweights.

Figure 7:
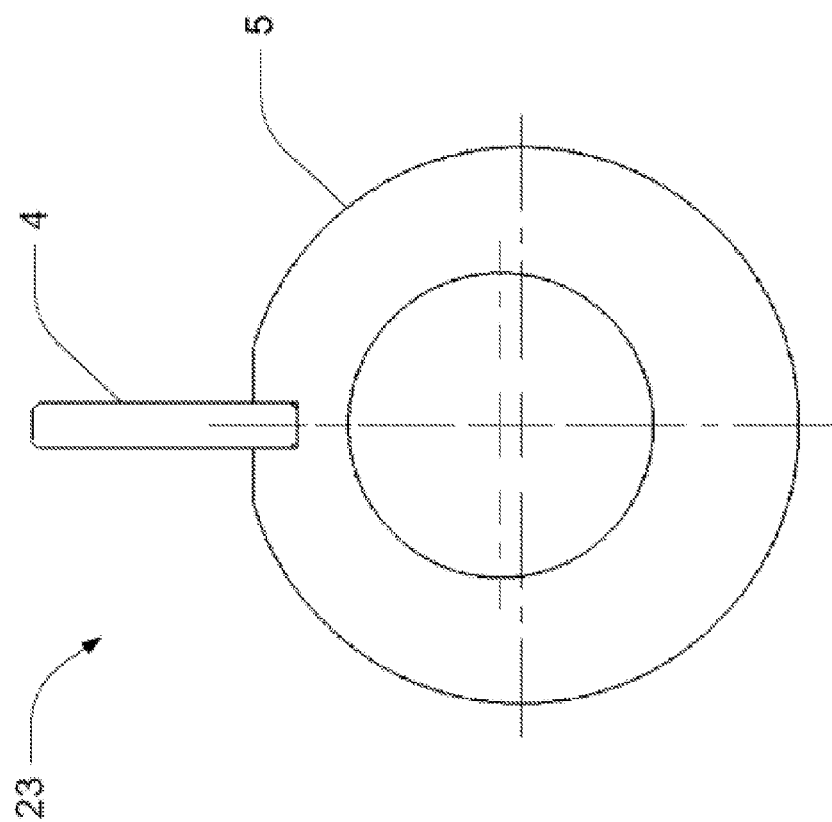
FIG. 7 shows a front elevated view of another implementation of a piston with a vane.

Accordingly, in another implementation of the present disclosure, as shown in FIG. 7, the piston 5 is balanced. For example, as depicted the hole in the center of the piston 5 is shifted radially, upward, toward the vane 4, such that the centerline of the hole is coincident with the center of mass of the part. Specifically, as depicted, the inside diameter of the piston 5 is shifted toward the vane, e.g., upwards. Hence, the inside and outside diameters of the piston 5 are not concentric. The center of mass of the vaned piston 23 is therefore centered within the geometric center of the interior diameter of the piston 5. The amount shifting is exaggerated in the figure. This arrangement allows simple counterweights to fully correct the imbalance caused by the eccentric motion of the piston mass. This configuration, therefore, reduces vibration and thereby reduces noise and wear on the component parts. Hence, in certain implementations, the compressor includes a piston 5 that is configured such that the center of mass of the piston and the vane combination 23 is coincident with the orbital circle of the piston.

Further, in certain implementations, the piston 5 includes one or more cutout portions, such as where the cutout portion does not intersect the outer periphery of the piston. In some implementations, the cutout forms a chamber, such as in an axial surface of the piston wherein the chamber includes an accumulator volume. In some implementations, the chamber is configured such that the accumulator volume is in communication with one or more of the suction chamber and/or the compression chamber. In some implementations, the chamber is configured such that the accumulator volume does not affect the compressor displacement volume and in other implementations, the cutout decreases the compressor displacement volume. In various implementations, the piston 5 and/or the one or more chambers are configured to facilitate a rise in static pressure between the endplate and the axial piston surface so as to maintain clearance between the endplate and the axial piston surface.

Figure 8:
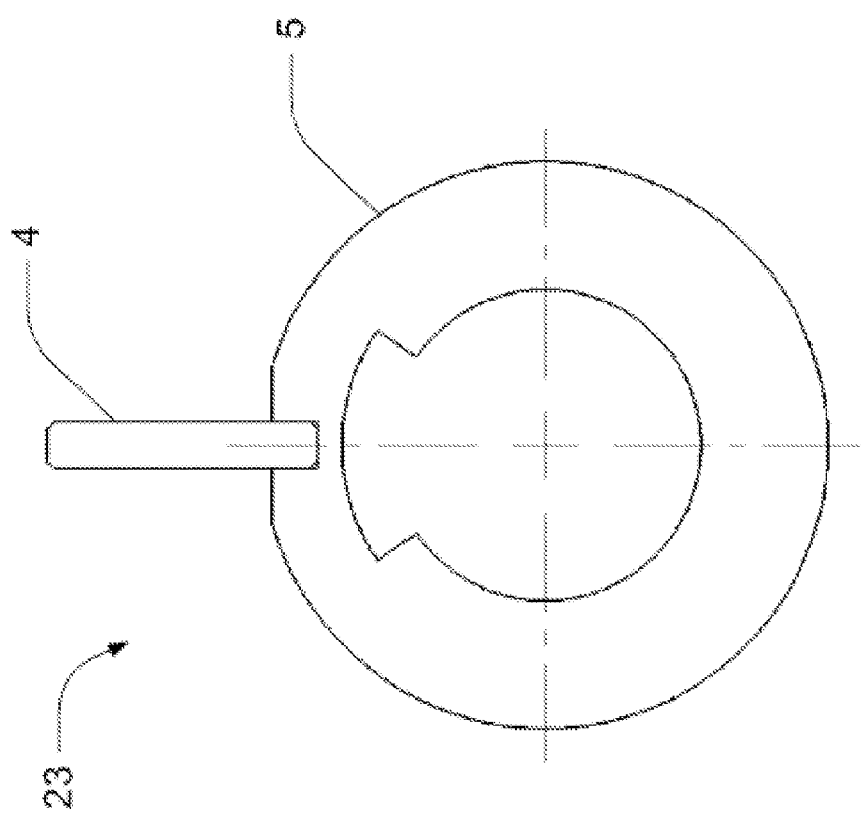
FIG. 8 shows a front elevated view of a further implementation of a piston with a vane.
Figure 9:
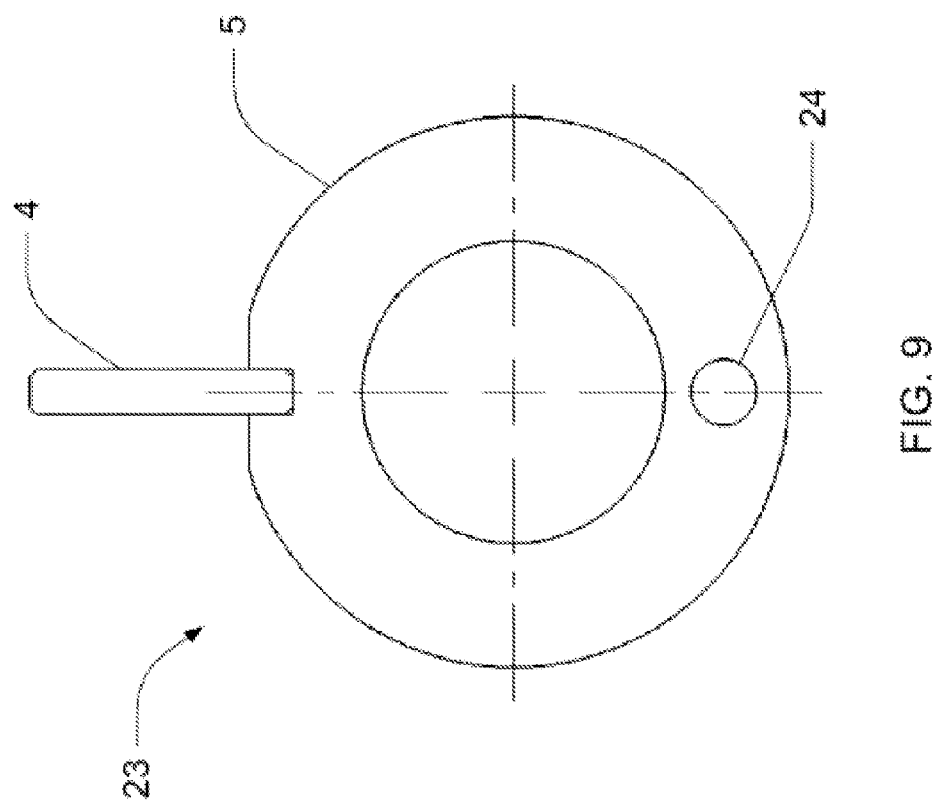
FIG. 9 shows a front elevated view of a still further implementation of a piston with a vane.

FIG. 8 shows another implementation for achieving the above benefits, namely, where material is removed from the piston 5 inside diameter so that the center of mass remains at the inside diameter geometric center line. Other modifications could achieve the same results, such as, by adding a high density insert 24 to the piston opposite the vane as shown in FIG. 9. Any number of modifications of the implementations shown in FIGS. 8 and 9 could achieve the same results. For example, a plurality of cutouts in the piston above the horizontal centerline could be used to achieve the same effect. These cutouts could, for example, be filled with a low density insert or could be left open. In general, it is desirable for the center of mass of the vaned piston 23 to be coincident with the orbit circle of the piston 5, centered at the bore chamber centerline. In practice, design constraints or manufacturing tolerances can result in deviations from the ideal. For example, a relatively large cutout portion for balancing the piston 5 and vane combination 4 may result in a piston that is structurally weak. Even so, a smaller cutout portion can still reduce imbalance. Therefore, for the purpose of this disclosure a balanced piston 5 and vane 4 combination is one in which the average distance of the center of mass from the orbit circle is less than it would be without the balancing feature as described above.

Figure 10:
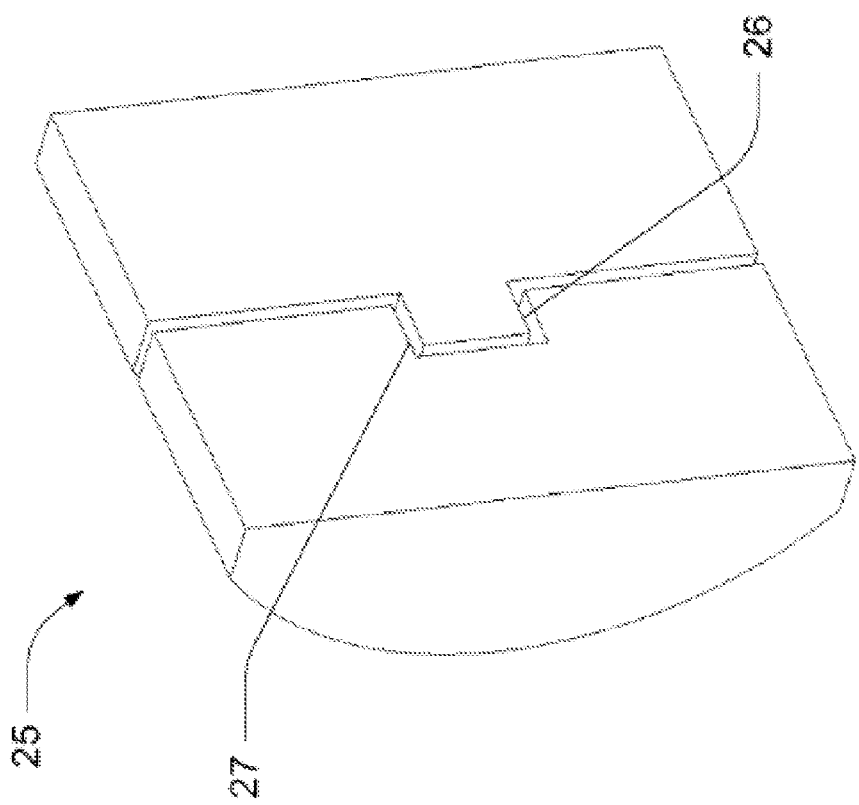
FIG. 10 shows a perspective view of an implementation of a bushing for the rotary compressor.

FIG. 10 shows an implementation of a bushing for use in a rotary compressor of the disclosure. In a typical lubricated rotary compressor, the liquid lubricant seals leakage gaps between adjacent parts that surround the compression space. This is true for the leakage path that exists between the bushings 3 and the endplates 17 and 18. For an oil free compressor, leakage gaps have to be very small or a contacting seal needs to be used. Keeping the leakage gap between the bushings 3 and endplates acceptably small requires very precise machining, which is expensive. Also, the material used for the bushing is not necessarily the same as the material used for the stator 2 and vane 4. Therefore, thermal effects may cause the clearance to vary during operation.

Accordingly, a multi-piece bushing design has been developed. The two piece bushing design 25 shown in FIG. 10 overcomes these challenges. The tongue 26 of a first bushing part and the groove 27 of a second bushing part in a two-piece bushing 25 acts in a manner similar to a piston ring, where the gas pressure between the two pieces act to push the bushing pieces apart allowing them to seal against the endplates. If useful a spring could also be used to bias the two halves of the bushing. The same pressure forces that push the bushing halves apart cause one surface of the tongue 26 and groove 27 to contact each other and provide a seal so that leakage between the two halves is minimal. This configuration is useful for promoting the sealing of the bushings with respect to the endplates. For example, the thickness of the bushings needs to be as thick as, but not thicker than, the thickness of the housing, e.g., stator, otherwise if the bushing is too thin, a leak path is generated allowing fluid to flow from the vane chamber 8 to the larger bore chamber 20, and/or if the bushing is too thick it prevents the endplates from properly sealing against the stator. The fluid pressure induced biasing force can be increased or decreased by adjusting the geometry of the tongue 26 and groove 27 and the location of the tongue 26 and groove 27, for example, changing the vertical position, as shown in FIG. 10.

Figure 11:
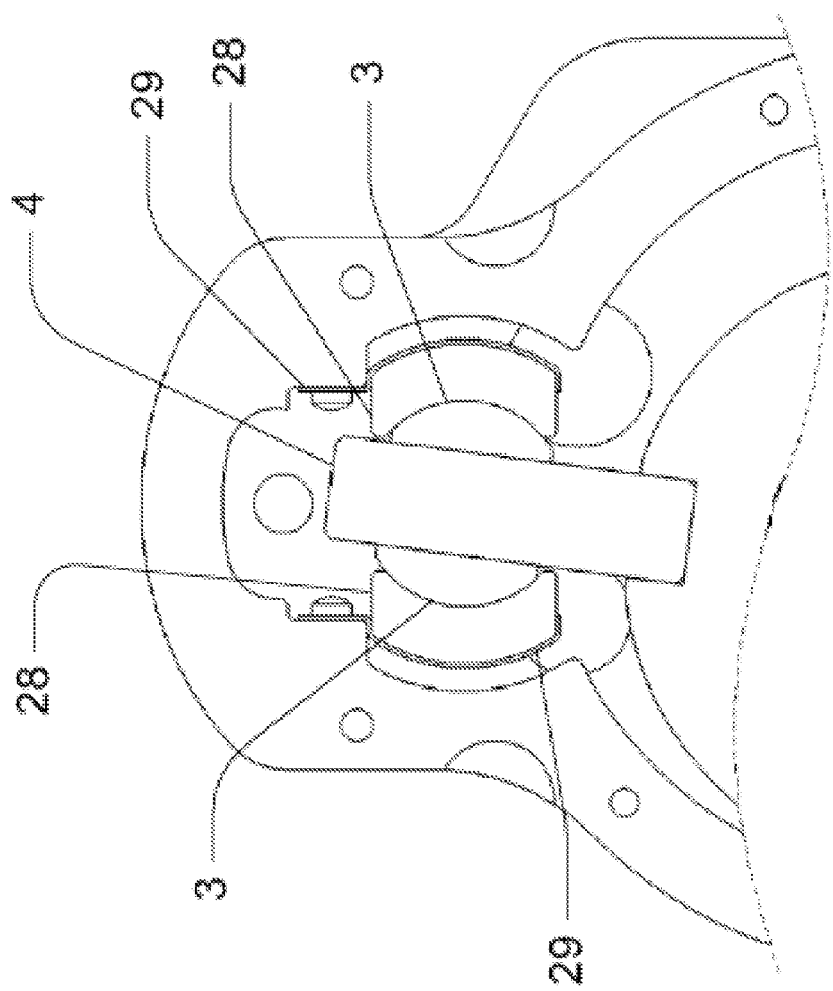
FIG. 11 shows a front elevated view of an implementation of a compliant bushing bearing.

FIG. 11 shows a compliant bushing bearing 28. Typically, bushing bearings are fixed structures. The disadvantage of this is that if the bushing bearing 28, bushing 3, or vane 4 wear, there are increased clearances between components that can lead to leakage, vibration, and noise. The compliant design uses a compliant member, such as a spring 29, or an elastomer, to bias the bushings 3 against the vane 4. A fixture can be included to hold the compliant member in place. Therefore, as wear occurs, the bushings 3, bushing bearings 28, and vane 4 remain in contact. Additionally, the compliance member may act to dampen vibration caused by the rotational motion of the piston, for example, by causing the vane 4 to stay more vertical. For example, during operation the piston 5 oscillates rotationally. This results in a torsional imbalance. The springs 29 or elastomer can be designed with the appropriate spring rate and damping force to counterbalance the torsional imbalance. As depicted only one compliance member is shown, however, two or more compliance members may be employed, for example, one on each side of the stator/bushing assembly.

Figure 12:
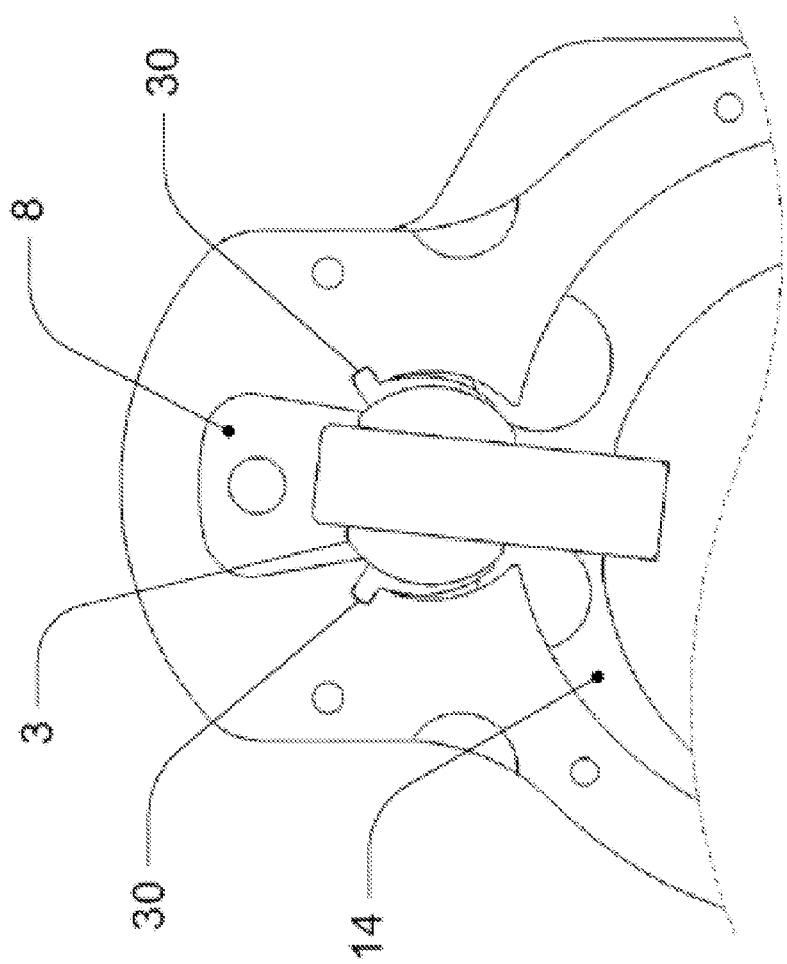
FIG. 12 shows a front elevated view of an implementation of a bushing bearing hinged on one end.

In FIG. 12 the bushing bearing 30 is hinged on one end, which end may be configured for being fitted within a complimentary receiving portion of the stator. In such an implementation, the fluid pressure difference between the vane chamber 8 and compression chamber 14 is used to bias the bushing bearing 30 against the bushing 3 so as to keep the bushing firmly pressed against the vane and so that wear of components can be tolerated, especially given the various chamber pressure differentials.

Figure 13:
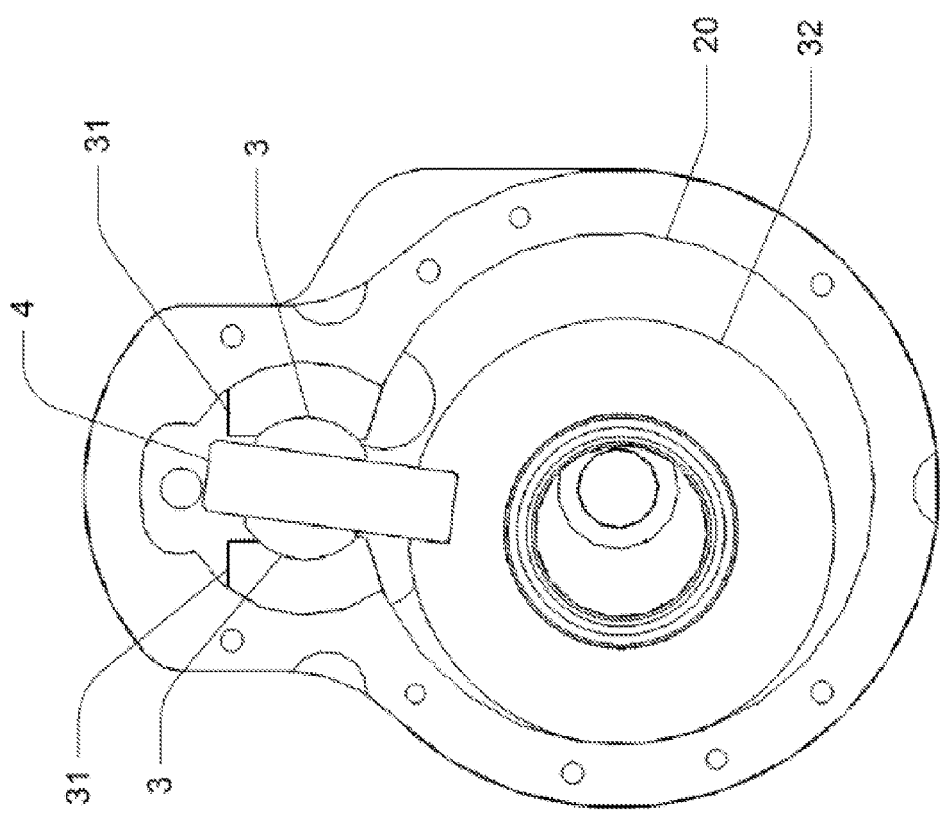
FIG. 13 shows a front elevated view of another implementation of a rotary compressor.

FIG. 13 discloses another implementation of the rotary compressor. In this implementation, the vane 4 and/or bushing bearings 31 are fabricated from a highly wear resistant material, which is different from the base material of the stator and/or piston. Alumina and other such hard materials are very wear resistant. However, the cost of making the entire compressor out of such hard materials like alumina would be very high. Aluminum, on the other hand, is relatively inexpensive, but if the vane 4, bushings 3, and bushing bearing were all fabricated from aluminum, liquid lubrication would be required to achieve reasonable reliability. The use of hard inserts for the components that contact one another, in this implementation, the bushing bearing, provides a cost effective means for greatly reducing the compressor cost and improving reliability without requiring liquid lubrication. Alternatively, coatings such as diamond like carbon, and/or any fluoropolymer based coating (for example, low-friction and wear-resistant composites of fluoropolymers and reinforcing binder resins) could be applied to the same areas of the compressor. The bushing bearings 31, bushings 3 and vane 4 are not limited to being very hard materials. Certain plastic formulations with base resins such as polyimides, polyamide-imides, and polyether-ether-ketones have high wear resistance and lubricity under conditions of dry sliding contact.

In another implementation, also shown in FIG. 13, the outside diameter of the piston and/or the stator inside diameter 20 may be coated with an abradable coating. The thickness of the coating is such that a small interference exists between the piston outside diameter 32 and the stator inside diameter 20. This interference may exist for some orbital positions of the piston 5 or for all positions of the piston 5. During operation of the compressor the abradable coating wears off so that line to line contact is achieved between the components. This results in a very low leakage rate between these components as well as low frictional losses because contact is negligible. Abradable coatings may also be used on the axial faces of the piston and vane and/or endplates to achieve similar reductions in leakage across these surfaces. The use of abradable coatings may permit features of the compressor, for example, the piston outer diameter to be made with less precision without sacrificing efficiency because the abradable coatings wear away for near perfect mating. This may reduce the manufacturing cost of the compressor.

Figure 14:
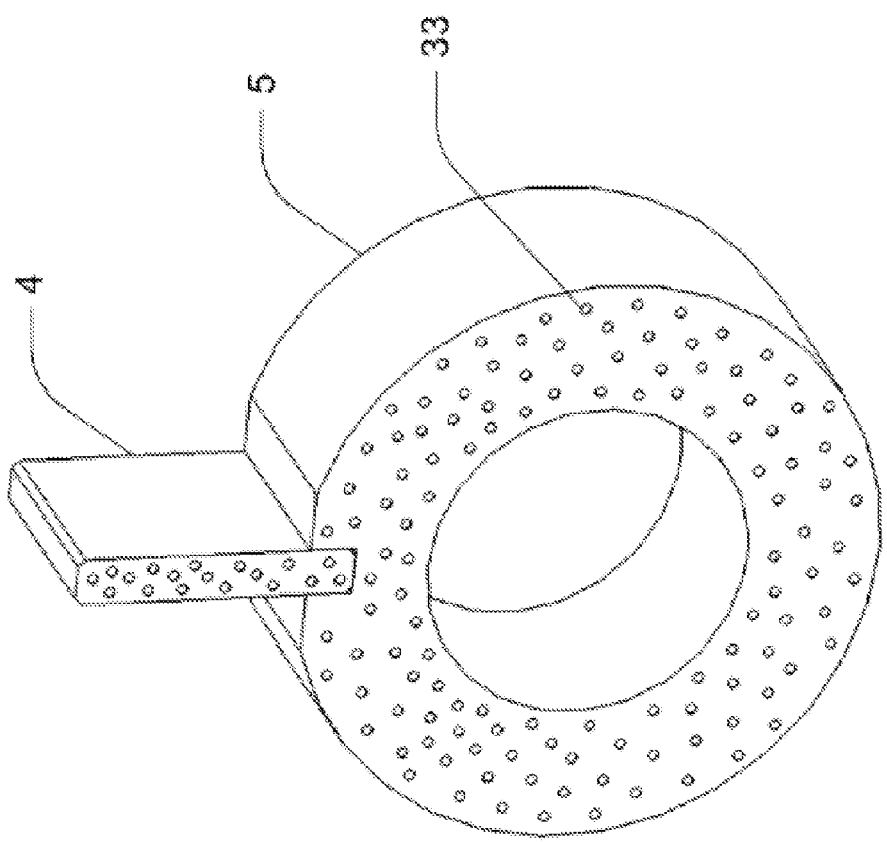
FIG. 14 shows a perspective view of another implementation of a piston with a vane and shows dimples added to the surfaces of the piston and vane.

FIG. 14 shows another implementation of the piston 5. Cut outs, such as shallow dimples 33 may be added to one or more of the surfaces of the piston 5 and/or vane 4 so as to form a fluid-dynamic bearing. Specifically, fluid fills the small clearance between the suction endplate 17, for example, and an axial face of the piston. When the piston 5 orbits, the dimples 33 cause a pressure rise of the fluid in the gap. This results in a force that pushes the piston 5 away from the endplate. The force decreases as the gap between the endplate and piston 5 increases. When dimples 33 are on both axial faces of the piston 5 the fluid-dynamic bearings tend to center the piston 5 between the endplates 17 and 18. This minimizes contact between the piston 5 and endplates, which can reduce wear and improve efficiency. Additionally, another purpose of the dimples is to make any leakage flow paths more arduous. The effect of this is that the mass flow rate of fluid through the leakage path is reduced. These modifications result in an efficiency improvement. The inside surface of the endplates, piston 5 outside diameter, and/or stator inside diameter 20 may also be dimpled to achieve the same effect. Other surface modifications may be used. For example, the surface could be bead blasted or radial cutouts could be used to achieve a similar effect.

Figure 15:
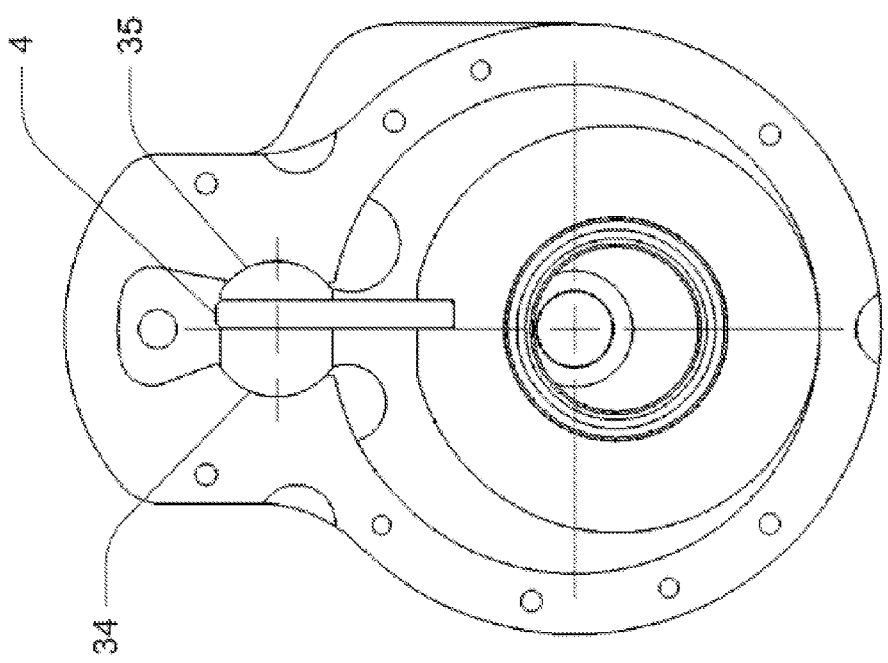
FIG. 15 shows a front elevated view of a portion of an implementation of a rotary compressor and shows a compression side bushing larger than a suction side bushing.

FIG. 15 shows a portion of a rotary compressor where the compression side bushing 34 is of a different size, e.g., larger, than the suction side bushing 35. Specifically, the radius of the compression side bushing 34 extends for more degrees of arc than the suction side bushing 35. Accordingly, when the vane 4 moves in and out of the slot created by bushings 34 and 35, friction tends to drag the bushing in the same direction as the vane motion. When this occurs the bushings tend to act as wedges between the bushing bearings 36 and 37. This can cause binding to occur especially as parts wear. The problem of binding primarily tends to affect the compression side bushing 34 more than the suction side bushing 35; therefore, it is advantageous to make the compression side bushing 34 larger. However, in some implementations, this configuration may be reversed as desired, for example, in configurations where bushing 35 tends to wear faster than bushing 34.

Figure 16:
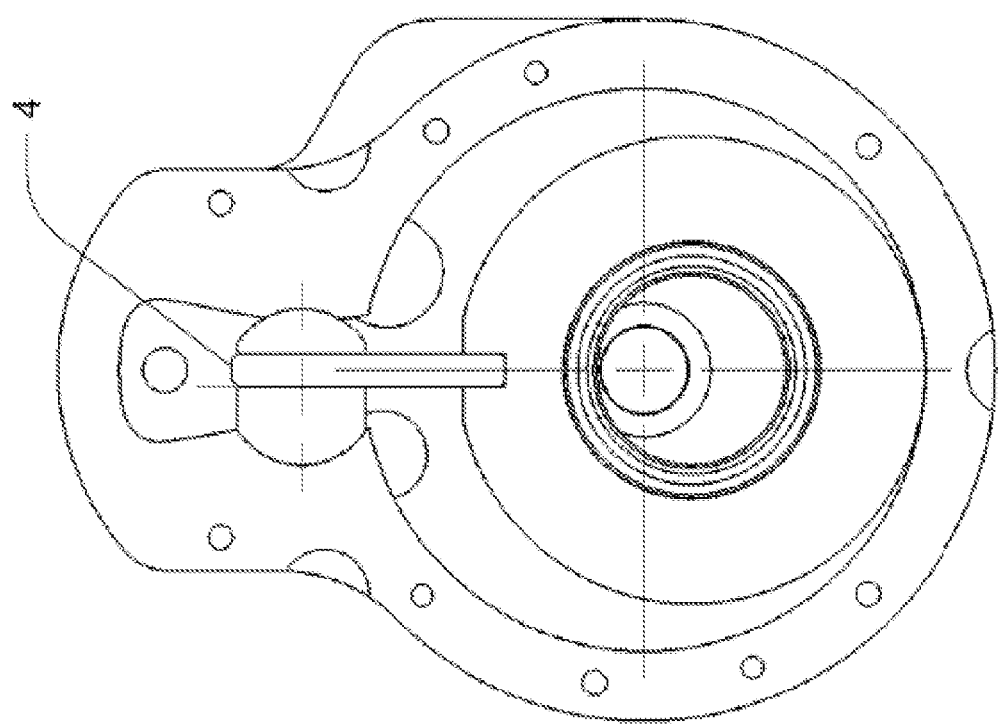
FIG. 16 shows a front elevated view of a portion of another implementation of a rotary compressor and shows different size bushings.

FIG. 16 shows another implementation of the rotary compressor 1 with different size bushings. In this implementation, the vane 4 remains symmetric with respect to bisecting the piston. As depicted the bushing and bearing have been shifted to the left, whereas in FIG. 15 the vane 4 is off center, e.g., positioned right of the center line of the piston.

Figure 17:
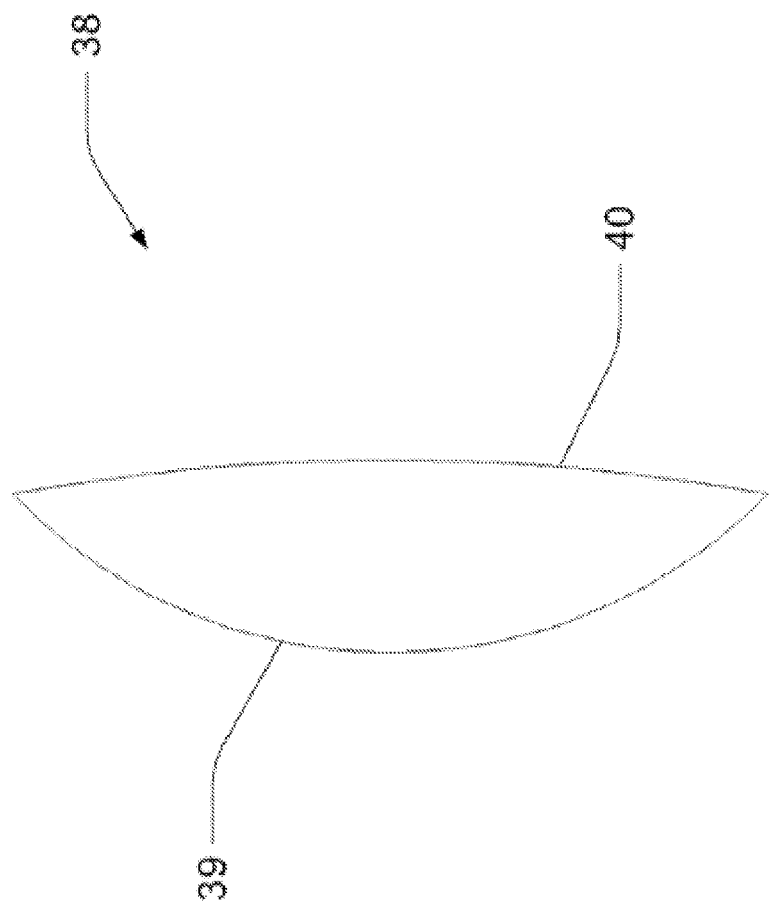
FIG. 17 shows a front elevated view of an implementation of a bushing.

FIG. 17 shows another implementation of the bushings 38. In this implementation the bushing 38 shown has a radius 40 on the surface which is curved, whereas typically this surface is flat. The journal radius 39 mates with the bushing bearing in the typical manner. The curved radius 40 has several advantages. For example, it helps direct the forces that act on the vane 4 and bushing 3. For example, for a given vane 4 thickness and journal radius 39 the radius 40 decreases the mechanical advantage of the bushing with respect to its ability to bind the vane 4. Hence, this configuration gives the bushing a geometry that is tolerant of wear, and dependent on the bias of the curvature of 40 (proximal or distal with respect to the piston), the mechanical advantage may be adjusted upwards or downwards.

Figure 18:
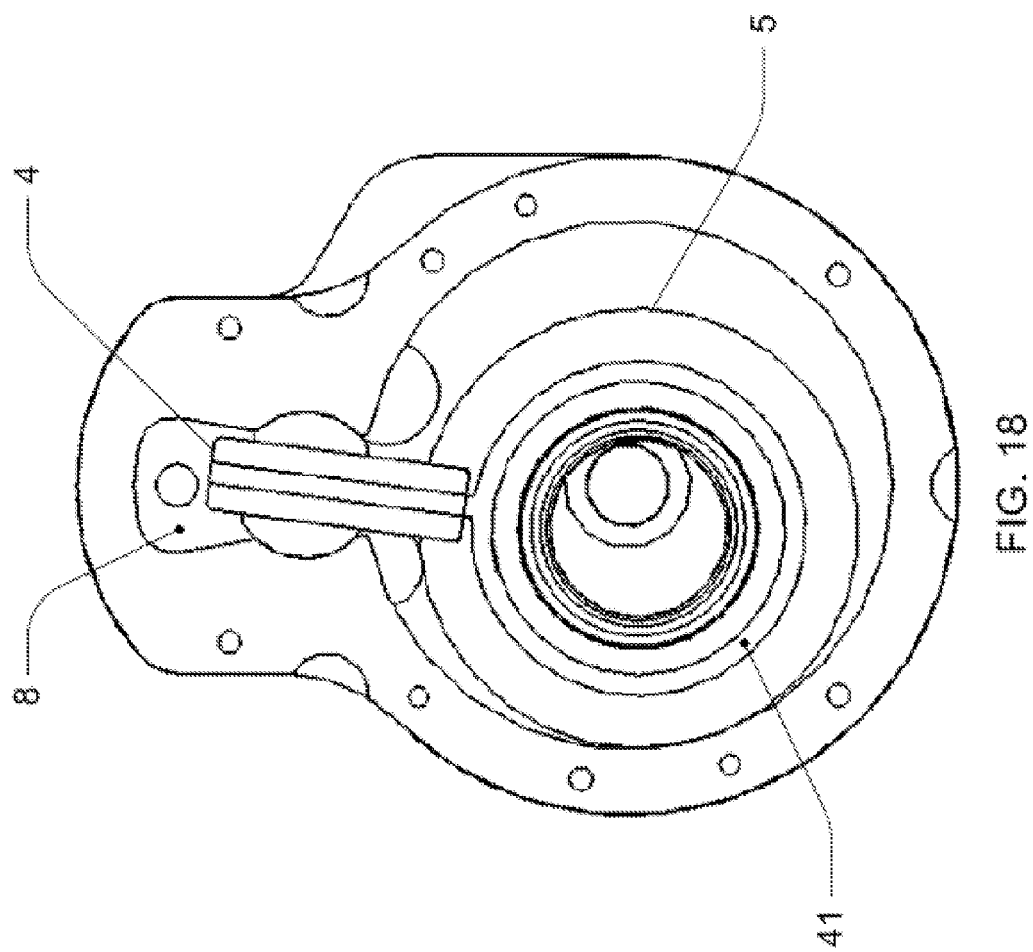
FIG. 18 shows a front elevated view of a further implementation of a rotary compressor.

FIG. 18 shows another implementation of the rotary compressor. In this implementation, a shallow recess is cut into the vane 4 which is coincident with a shallow recess cut into the piston 5. Hence, compressed gas from the vane chamber 8 is in fluid communication with the recesses in the vane 4 and axial face of the piston 5. The opposing axial faces of the piston 5 and vane 4 may have a similar feature. The pressure of the fluid in the recesses 41 keeps the piston 5 from contacting the endplates in a manner similar to the implementation disclosed in FIG. 5. Other configurations for the flow passages are also possible.

Figure 19:
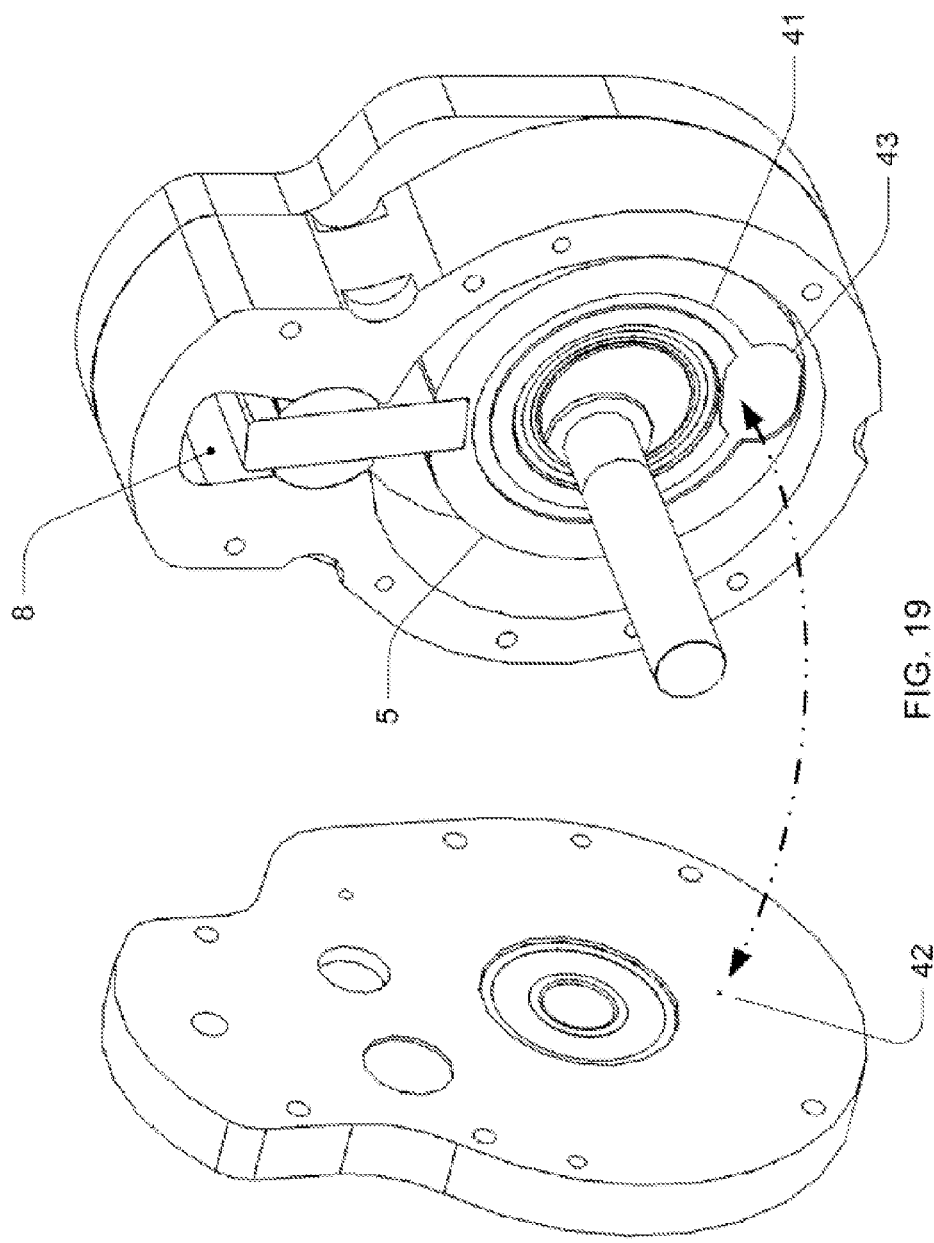
FIG. 19 shows an exploded perspective view of a still further implementation of a rotary compressor.

FIG. 19 shows a similar implementation where the fluid is fed from ports in the endplates (not shown). The recess 41 can be positioned in the endplates or both the endplates and pistons. The port 42 in the endplate is shown where it intersects the recess 41 at enlarged pocket 43 in the piston 5. In a manner such as this, the recess 41 may be pressurized so as to form an air bearing which functions to keep the piston 5 centered axially between opposing endplates.

Figure 20:
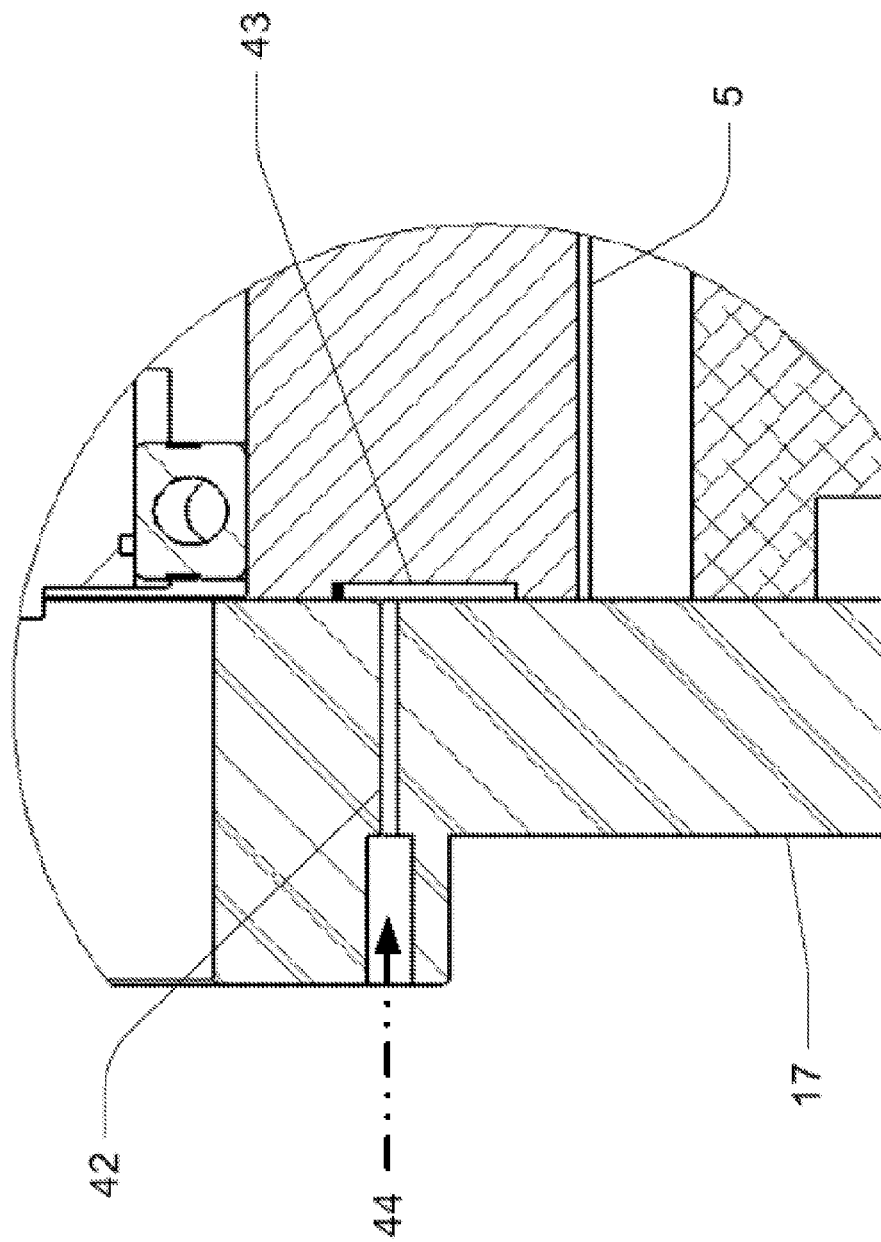
FIG. 20 shows a cross-sectional view of a section of an implementation of a discharge endplate and a piston.

FIG. 20 shows a section of the discharge endplate 17 and piston 5 where fluid 44 is in communication with the recess 41 at pocket 43 via port 42. In some implementations, at least one endplate includes a chamber. The chamber can include a cutout portion, such as a cutout portion that is adjacent to an axial surface of the piston and/or configured to facilitate a rise in static pressure between the endplate and the axial surface of the piston. The chamber may form a port, where the port may be in fluid communication with the chamber on the surface of the piston 5. A fluid pressure source may be connected to the port such that the pressure source is communicated to the chamber for at least a portion of the piston's orbit. One endplate may include the chamber, and the second endplate may include the discharge port, such as where the discharge port is in axial opposition to the chamber. The chamber of the piston 5 can extend from one axial surface to another axial surface of the piston, thereby providing fluid communication between axial surfaces of the piston. The chamber can function to equalize pressure between either end of the endplate.

Figure 21:
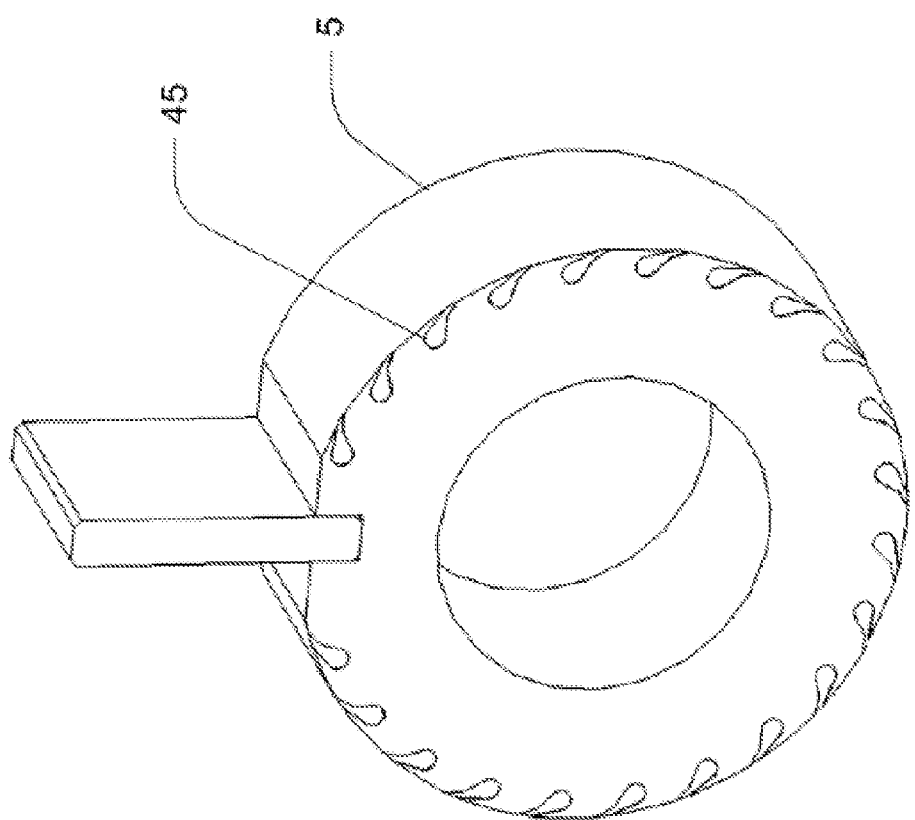
FIG. 21 shows a perspective view of another implementation of a piston with a vane and shows an implementation for floating the piston.

FIG. 21 shows another implementation for balancing the piston 5 axially, wherein the balancing involves floating of the piston 5. Cut outs or recesses 45 intersect the outside diameter of the piston 5. The motion of the piston 5 causes the recesses 45 to pressurize and dynamically compresses the fluid in the recess 45. One or both sides of the piston 5 may include recesses 45. The velocity head is converted to static pressure head via diffusion. This keeps the piston 5 from contacting the endplates in a manner similar to the implementation disclosed in FIG. 14.

FIG. 22 shows an implementation where a sensor 71 is placed in communication with the compression chamber 14 and a fluid pressure source 72 is placed in fluid communication with the vane chamber 8 via a controller 73 so as to control pressure in the vane chamber 8 and improve efficiency and/or decrease wear. The signal 74 from the sensor is used to command the controller to variably apply pressure from a fluid pressure source to the vane chamber 8. The controller 73 may be any suitable controller and may take the form of a mechanical system (for example, a pneumatic system, a valving system with valves, and the like), an electromechanical valve, and/or a computer. Any mechanism for controlling the vane chamber pressure as a function of crank-angle may be employed. The sensor 71 may be a proximity sensor, a pressure sensor, a hall-effect sensor, or any other type of sensor that conveys pressure and/or position data.

Figure 23:
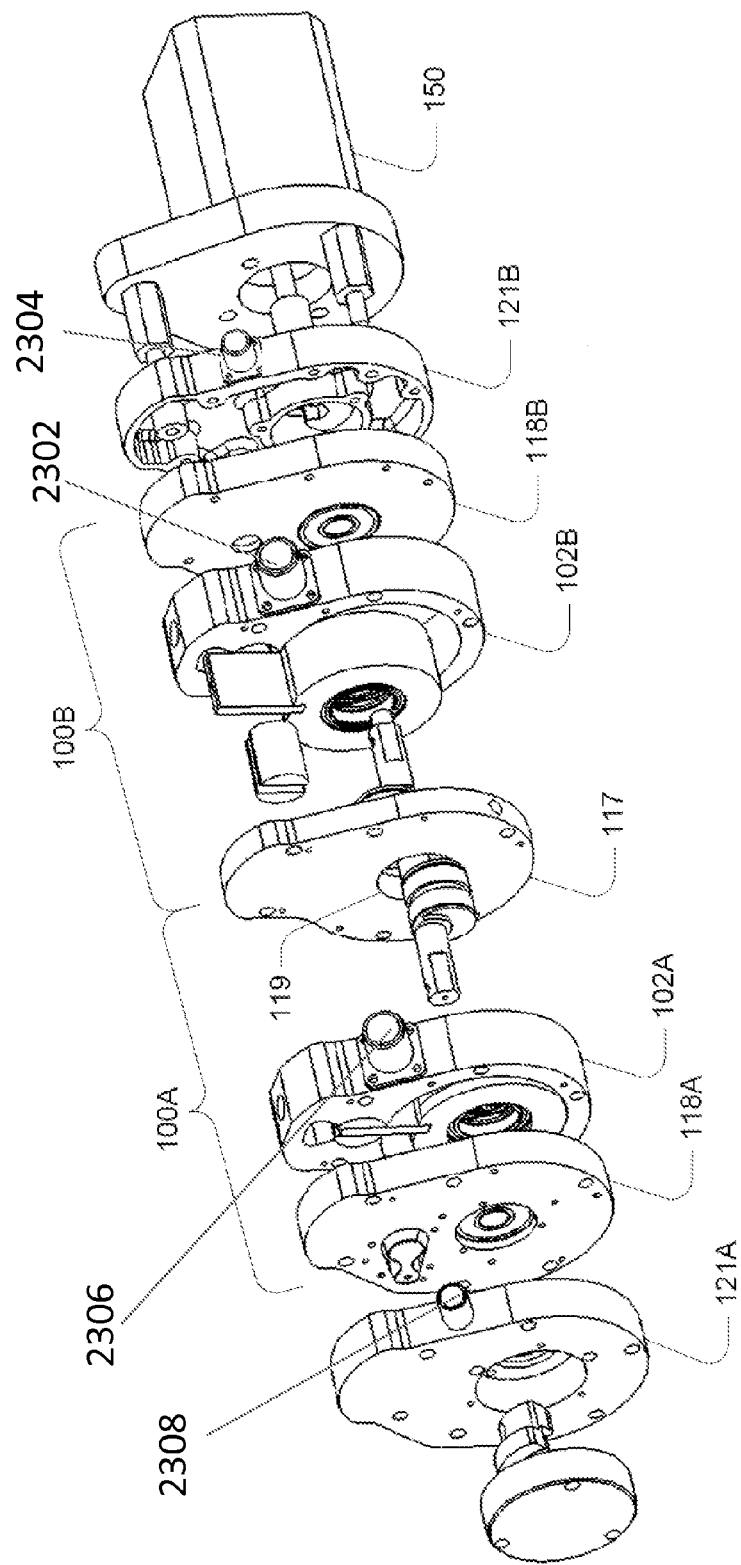
FIG. 23 shows an exploded perspective view showing two rotary compressors operated by a single motor.

FIG. 23 shows an implementation where two systems 100A and 100B are driven by a single motor 150. The system 100A includes a stator/housing 102A, which is positioned between two endplates 118A and 117. The second system 100B includes a stator/housing 102B, which is also positioned between two endplates 118B and 117. Both systems 100A and 100B share the common endplate 117. In alternate implementations, each system 100A and 100B can have its own corresponding non-shared endplates. The system 100A is connected to a muffler 121A, and the system 100B is connected to a muffler 121B. The systems 100A and 100B are driven by a single motor. One of the two systems 100A and 100B may act to increase pressure above ambient pressure, and other system of those two systems 100A and 100B may act to reduce pressure below ambient pressure. For example, system 100B may be configured to function as a compressor, and system 100A may be configured to function as a vacuum pump. Each of the system 100A and 100B can be configured to function as either a compressor or a vacuum pump. In some implementations, both systems 100A and 100B can be compressors.

Now, transmission of fluids is described when system 100B functions as a compressor, and system 100A functions as a vacuum pump. The system 100B includes a first inlet 2302, and the muffler 121B includes a first outlet 2304. The system 100A includes a second inlet 2306, and muffler 121A includes a second outlet 2308. The first inlet 2302 can receive ambient air, which is then pressurized by the system 100B functioning as a compressor. The first outlet 2304 can send this pressurized air to a separator, which can separate oxygen from other gases, including nitrogen and argon. The oxygen can then be provided to patients requiring oxygen. The separator can perform either pressure-swing-adsorption (PSA) or vacuum-pressure-swing-adsorption (VPSA) to separate oxygen from other gases in ambient air. The second inlet 2306 can receive (for example, pull-in), from the separator, other gases separated by the separator, such as nitrogen and argon. The second outlet 2308 can then exhaust out these other gases.

In some implementations, gas can leak into an endplate chamber 119. Gas that leaks into the endplate chamber 119 from the pressure system is hot and at a high pressure. This gas tends to be drawn from system 110B functioning as a compressor into system 110A functioning as the vacuum pump, thereby reducing efficiency. In some cases, the leak rate from the system 100A functioning as vacuum pump can be high. The high leak rate of the system 110A functioning as a vacuum pump can lower the pressure in the endplate chamber 119, thereby increasing the leak rate from the system 110B functioning as a compressor. However, to prevent or minimize this leakage, a vent hole 125 can be positioned in the shared endplate 117 in order to keep the endplate chamber 119 at an optimal pressure. This optimal pressure may be ambient pressure or some other pressure and/or may be from another source. The optimal pressure of the endplate chamber 119 prevents the shared fluid exchange between the systems 110A and 110B, and reduces the effects of the pressure of one system from having deleterious effects on the other system.

FIG. 23a shows a cross-sectional view showing two rotary compressors operated by a single motor.

Figure 23B:
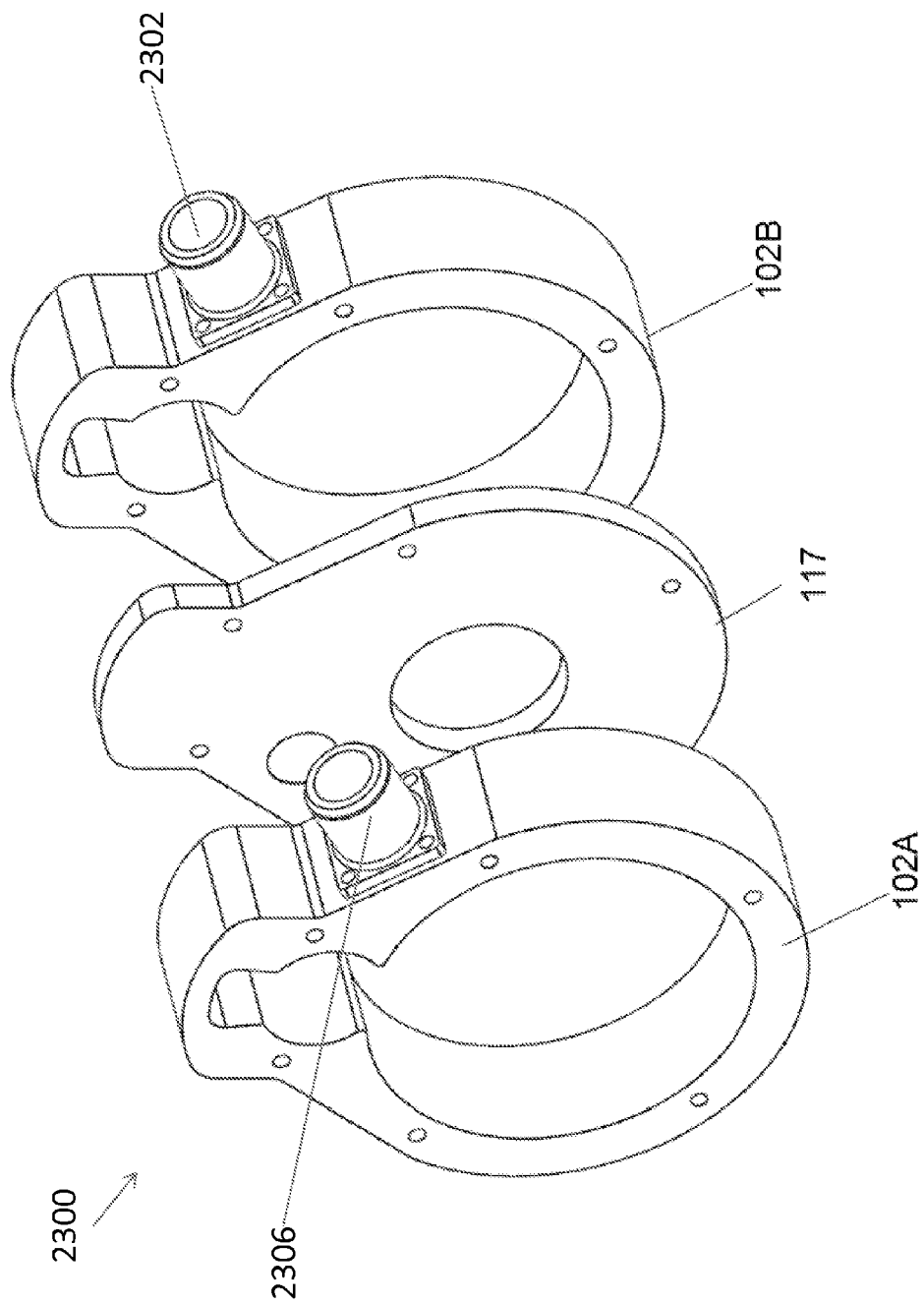
FIG. 23b shows an expanded view of one example of the stator assembly.

FIG. 23b shows an expanded view of one example of the stator assembly 2300, as also shown in FIG. 23. The stator assembly 2300 includes a stator 102A and a stator 102B that can be connected via an endplate 117. The stators 102A, 102B, and the endplate 117 need to be aligned together accurately before combining.

Figure 23C:
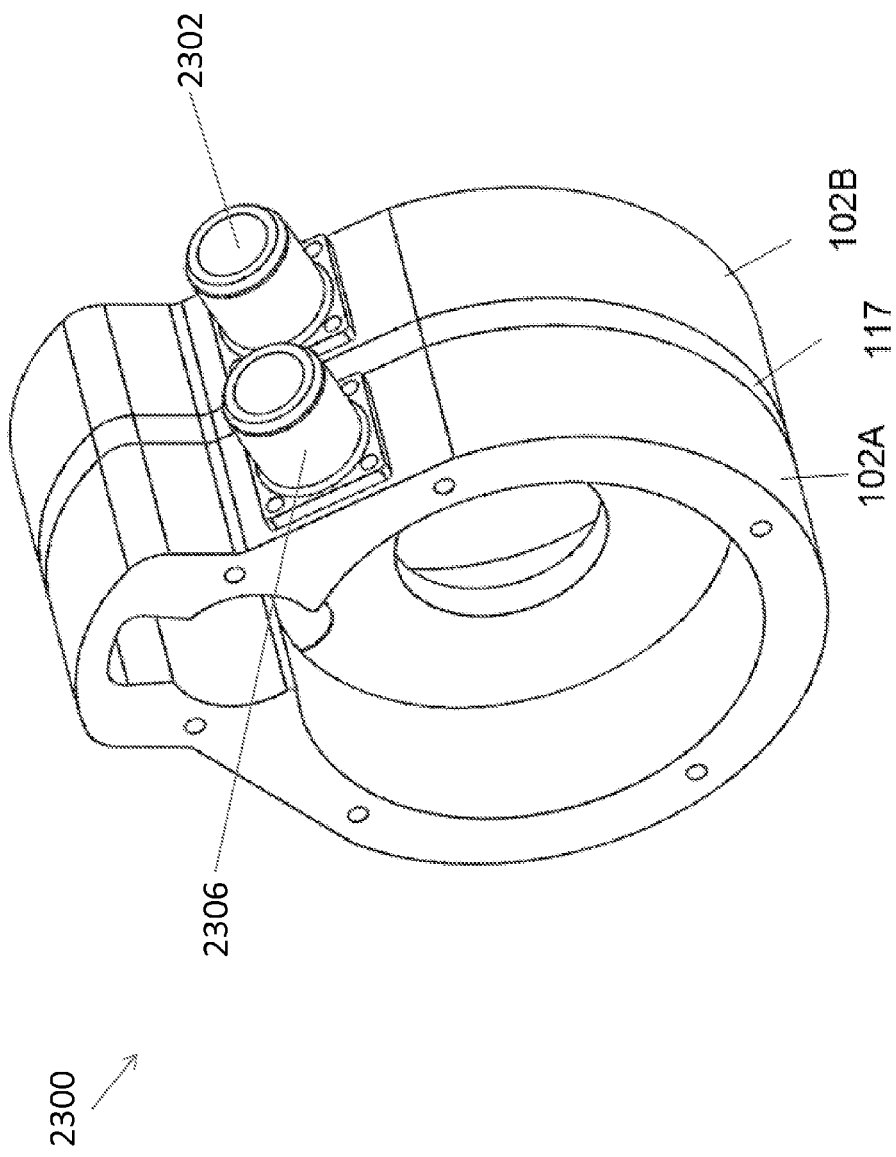
FIG. 23c shows the stator assembly where the stators and the endplate have been combined.

FIG. 23c shows the stator assembly 2300 where the stators 102A, 102B, and the endplate 117 have been combined. As noted above, this combination requires the stators 102A, 102B, and the endplate 117 to be aligned together accurately before combining.

Figure 23D:
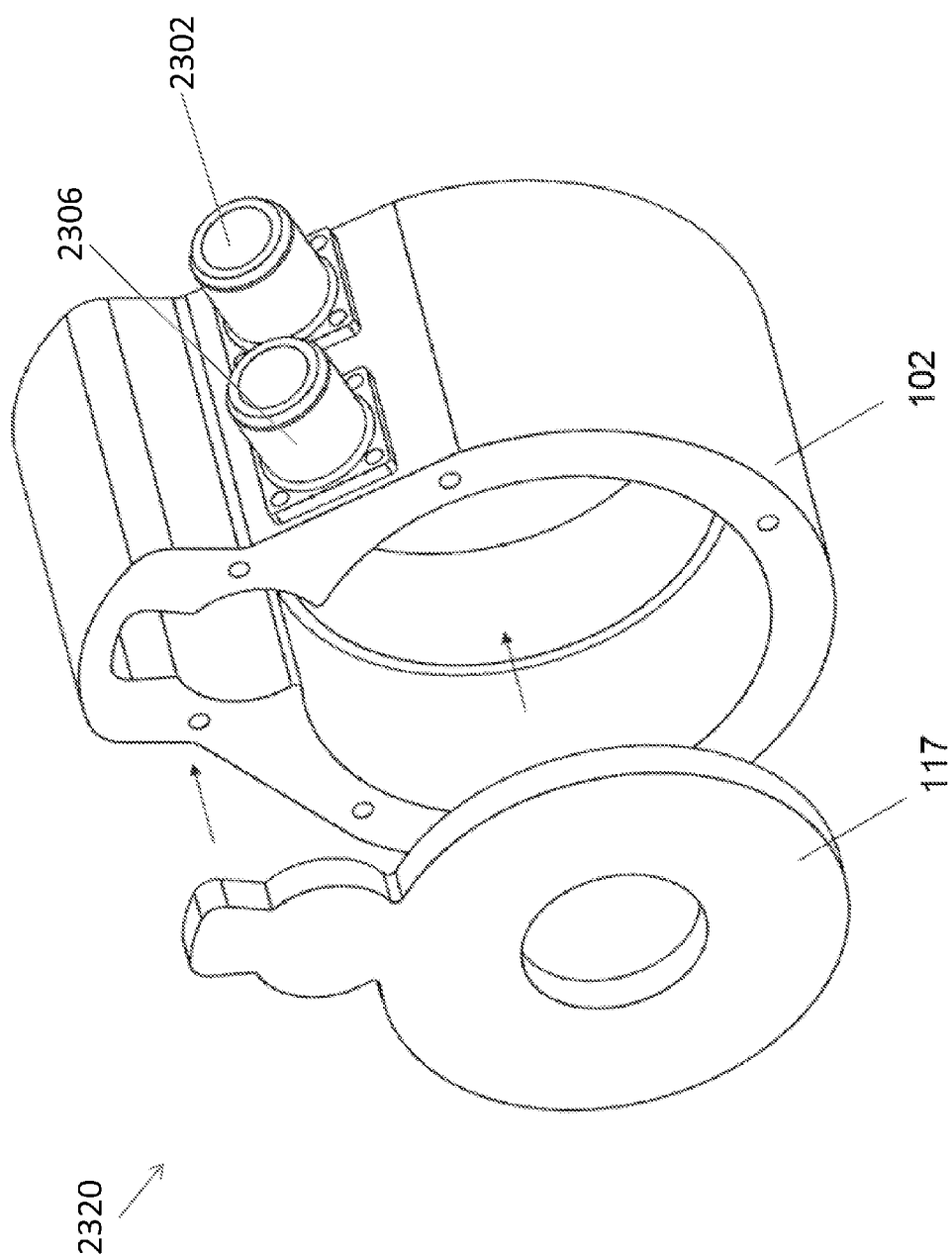
FIG. 23d shows an expanded view of another example of the stator assembly.

FIG. 23d shows an expanded view of another example of the stator assembly 2320, which can be substituted instead of stator assembly 2300 described above. The stator 102 is a single machined unit. The endplate 117 is configured to slide inside, as shown, to separate the volume of the bore chamber into two separate bore chambers. Alternately, the stator 102 can be seen as two stators that are machined together and that allow the endplate 117 to pass through in order to create bore chambers of corresponding stators. In one implementation, both chambers can be used for compression. In another implementation, one chamber can be used for compression, and the other chamber can be used for vacuum. For a stator 102 where one chamber is configured to be used for compression and the other chamber is configured to be used for vacuum, one chamber can be larger than the other chamber, as piston displacement required to create fluid pressure flow for compression can be different (more specifically, significantly different in most situations) from the displacement required to create fluid pressure flow for vacuum.

The stator assembly 2320 can be advantageous over stator 2300, as the stator assembly 2320 prevents time spent during alignment of separate stators 102A and 102B of stator assembly 2300. Additionally, even when the separate stators of the stator assembly 2300 are aligned and attached, the alignment may not be proper, thereby causing an undesirable clearance issue, and therefore, interference and/or leakage. Other issues due to misalignment can also occur. However, stator assembly 2320 prevents such undesirable issues, as the stator 102 is a single machined unit and alignment (as required for stator assembly 2300) is not required.

In some implementations, the location of the first inlet 2302 (and the location of the first outlet 2304) can be moved to adjust timing of beginning of compression cycle for compressing the fluid. The first inlet 2302 and the first outlet 2304 can be configured to be moved mechanically by a user. In some implementations, the second inlet 2306 and/or the second outlet 2308 can also be moved by the user. The movement of these inlets and outlets can be one dimensional, such as just up and down along the circumference of a corresponding stator. In one implementation, where these inlets and outlets are on the endplates, the movement of these inlets and outlets can (additionally or alternately) be radial on the endplates. These inlets and outlets can be adjusted to correspondingly adjust the ratio of flow rates of corresponding fluids in the systems 100A and 100B. This adjustment of ratio of flow rates of corresponding fluids can be beneficial for a vacuum-pressure-swing-adsorption (VPSA) oxygen concentration device. Although the one dimensional and/or radial movement of the first inlet 2302 and the first outlet 2304 is being described here, such movements are also possible for other ports performing similar functions in other systems, such as the suction port 10 and the discharge port 19 described for other systems.

Figure 23E:
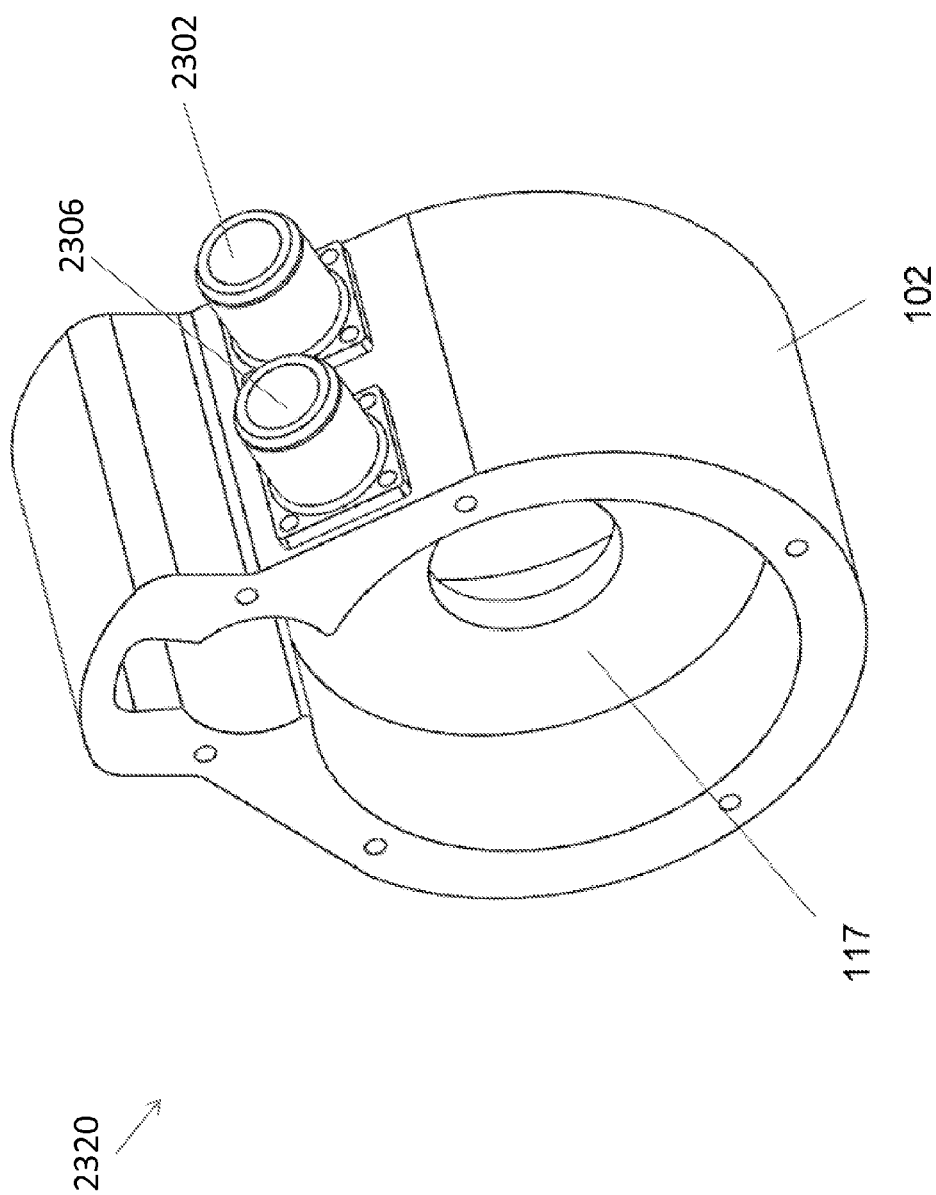
FIG. 23e shows the stator assembly where the endplate has been fitted inside the stator.

FIG. 23e shows the stator assembly 2320 where the endplate 117 has been fitted inside the stator 102.

Figure 23F:
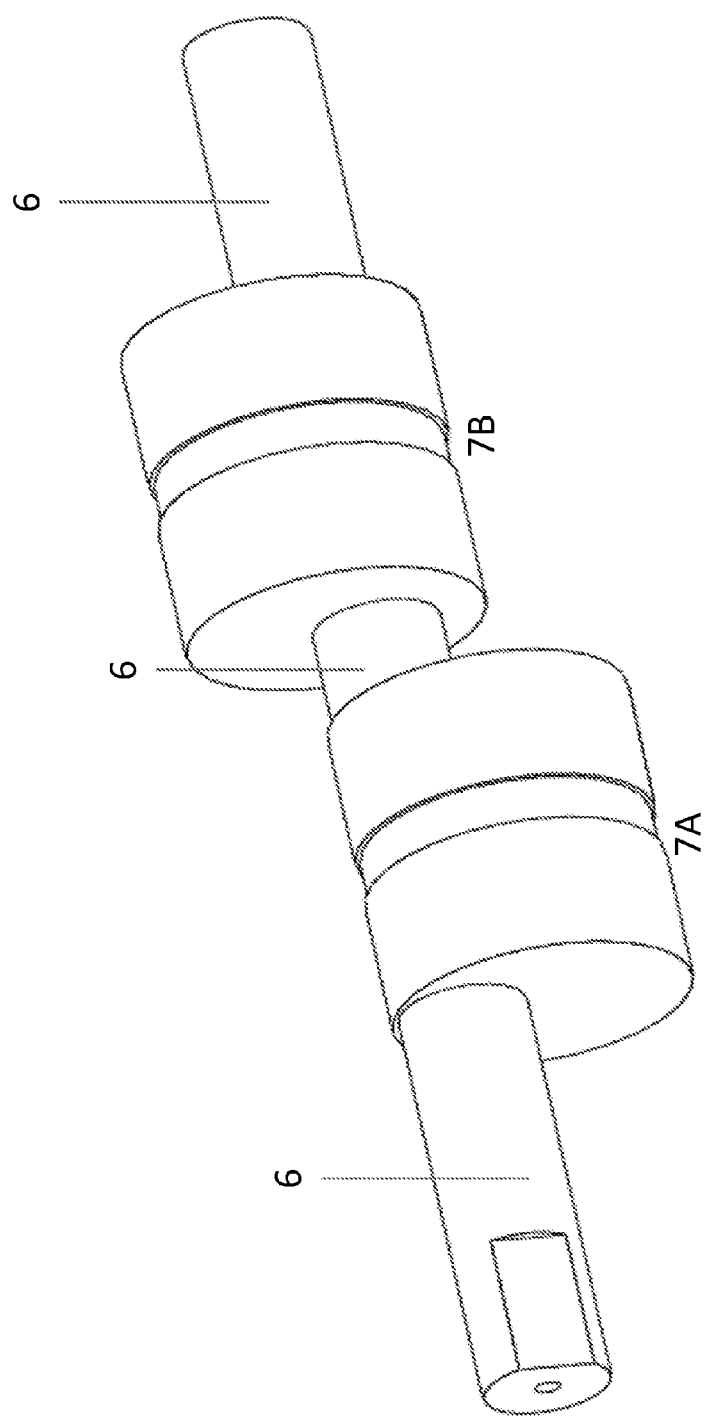
FIG. 23f shows the shaft with eccentrics for moving the pistons in separated bore chambers of stator of the stator assembly.

FIG. 23f shows the shaft 6 with eccentrics 7A and 7B for moving the pistons in separated bore chambers of stator 102 of the stator assembly 2320. Where one bore chamber of stator 102 is used for compression and the other bore chamber is used for vacuum, these bore chambers have different volumes, as different piston displacements are required for compression and vacuum. To enable these different piston displacements, the size of the two pistons is kept constant while the eccentricities of eccentrics 7A and 7B are changed.

In an alternate implementation, to enable these different piston displacements, the sizes of the pistons can be varied while keeping eccentricities of the eccentrics 7A and 7B constant.

Figure 24:
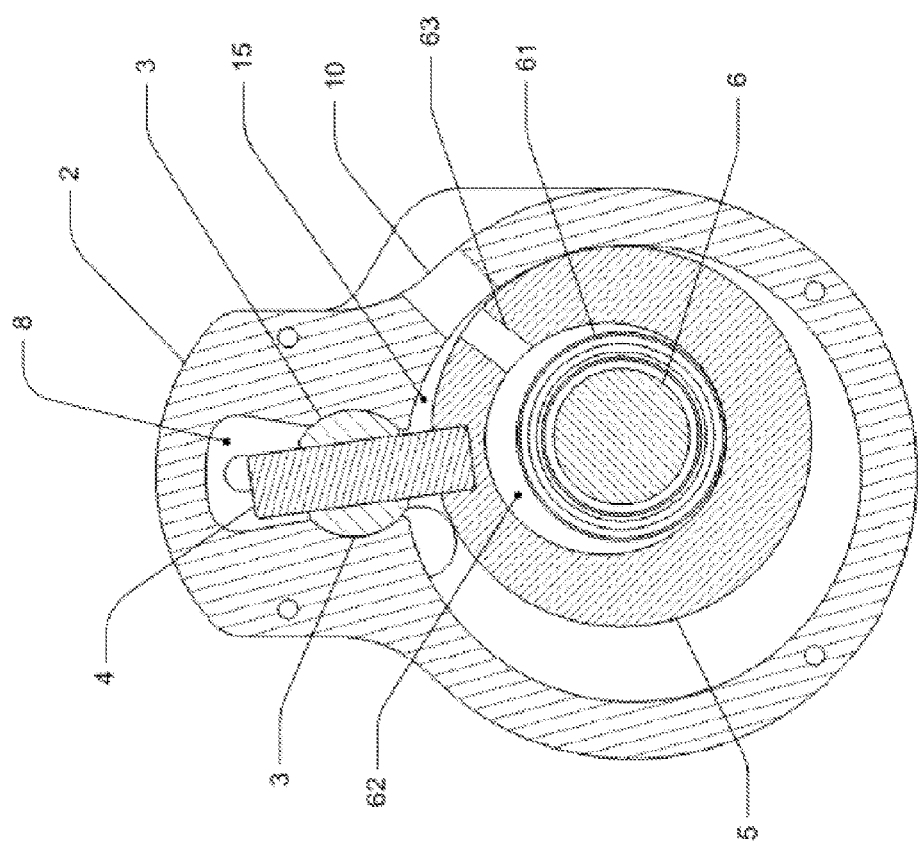
FIG. 24 shows a cross-sectional view of a rotary compressor showing a piston showing a cut-out section.

FIG. 24 provides another implementation of the rotary compressor. A stator 2 is provided. The stator 2 is associated with a bushing 3, a vane 4 and a piston 5. Also depicted are a shaft 6 having a bearing 61 associated therewith. As can be seen, in this implementation, stator 2 includes the inlet port 10. Further, in FIG. 24, a chamber 62 and passage 63 in the piston forms an accumulator volume. The accumulator volume may function in part to reduce inlet pulsation noise. For example, as the piston moves past the suction port 10 in the stator 2, the incoming flow is abruptly slowed. This inlet flow stagnation can result in pressure waves that can typically cause objectionable noise. This configuration of the piston accumulation volume and stator containing inlet port can reduce the abrupt slowing of the flow and thereby reduce objectionable noise. The accumulator volume can also be formed by modifying the stator 2 in the inlet area or by allowing fluid communication between the vane chamber 8 and suction chamber 15. Because the piston is moving relative to the stator, the inlet port is increasingly opened and closed in an equivalent manner to the manner described above.

FIGS. 25a and 25b are configurations for equalizing pressure on either side of a sealed bearing. As can be seen with respect to FIG. 25a a section view of a shaft 6 and a shaft eccentric 7 is presented. A vent hole 80 is shown in the shaft eccentric 7 and traversing laterally there through. Sealed bearings can often contain lubricant within the sealed volume surrounding the bearing balls or rollers. When mounted, such bearings can form part of an obstruction or pressure boundary in a structure. Because the seals of these bearings are not intended to maintain a pressure boundary, when a differential pressure is applied across the bearing, lubricant can leak out, which may contaminate the process fluid of the compressor.

Accordingly, in one method to prevent lubricant from leaking out, a path is created to give the fluid under the differential pressure an opportunity to equalize. In the case of radial bearings, for example, as can be used in a rotary piston compressor of the disclosure, FIG. 25a shows a shaft 6 where bearings 81 for a piston 5 mount on the large diameter eccentric 7 and the equalization path passes entirely through the large diameter eccentric 7 of the shaft 6. In this manner, the pressure on both sides of interior diameter of the piston remains the same on both sides so as to centralize the axial motion of the piston, and the bearings are prevented from leaking.

FIG. 25a shows a shaft 6 and eccentric 7 where there is a notch 82 in the shaft so as to allow a flow path to be present around the inner ring of the bearings 83. Specifically, in this geometry, a small path is made along the diameter of the shaft where a sealed bearing mounts. The path may be small enough to not degrade the fit between the inner race of the bearing and the shaft, yet large enough to allow pressure to equalize across the bearing at a satisfactory rate and thereby achieving the same benefits as described above.

FIG. 25b shows a shaft 6, having a shaft bearing 83 (as in 25a), and an endplate, having one or more (for example, three) cutouts 84 so that fluid can flow there through around the outer ring. Specifically, in this bearing mounting configuration, the outer race of a sealed bearing is mounted in an endplate or similar structure, and one or more small paths are made along the mounting diameter for the bearing in the endplate. The small paths need not intersect with the mounting diameter, but may alternately be proximate to the mounting diameter. Again the path may be small enough to not degrade the fit between the race and the endplate, but large enough to allow pressure to equalize across the bearing at a satisfactory rate.

Figure 25C:
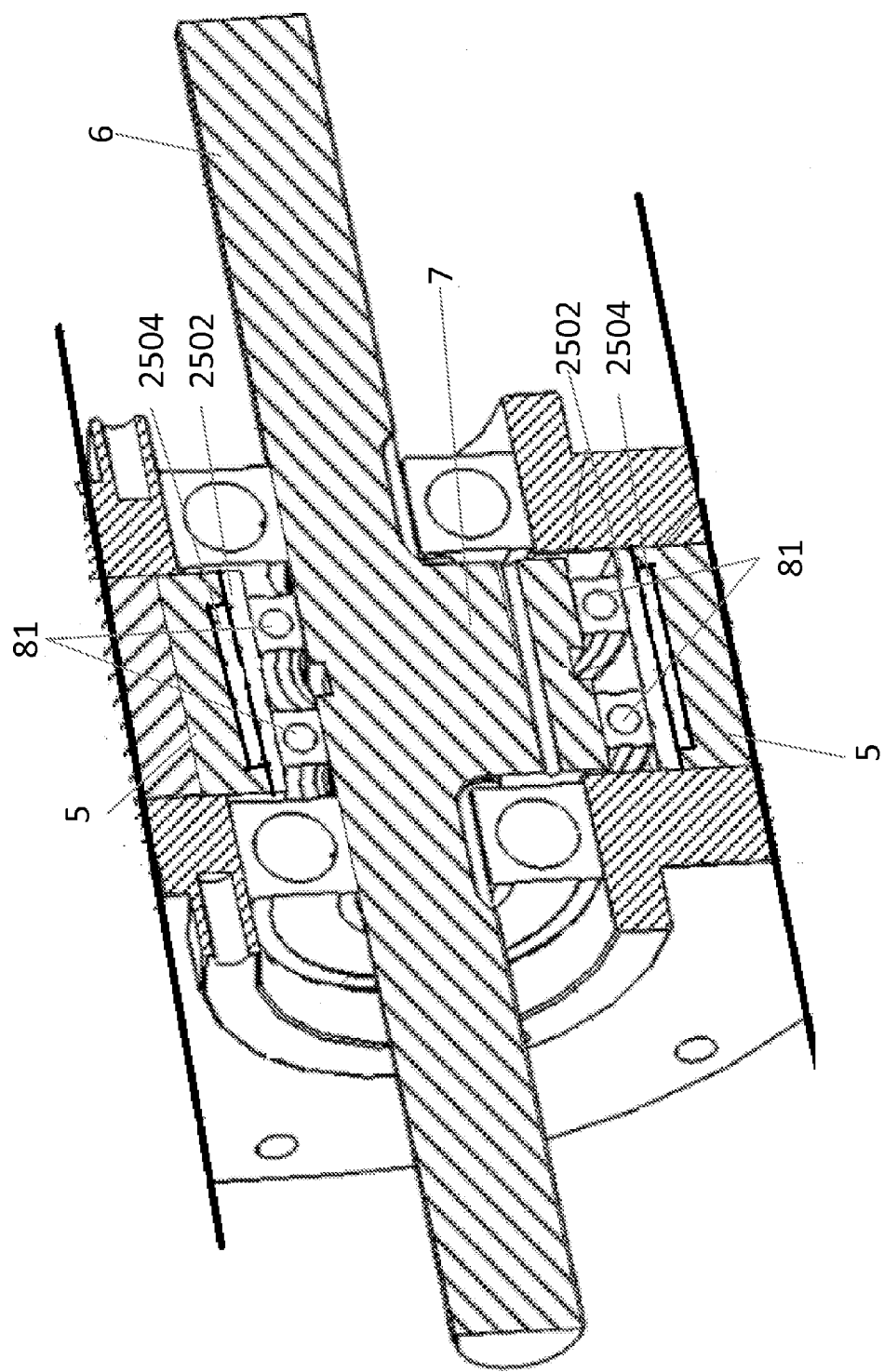

FIG. 25c shows a magnified view of a portion of the system shown in FIG. 25a. The inner surface of the piston is connected to an outside surface of the eccentric 7 by bearings 81. Although two bearings 81 are shown on eccentric 7, in other implementations, one bearing 81 may be present. The member 2502 between the bearings 81 and the piston can be the abradable coating (or other low friction materials discussed above), which can be formed of same material as that coated on the bushing bearings 31, as described above. As the eccentric 7 rotates, the bearings 81 push against the member 2502 due to the outward centrifugal force. The bearings 81 are configured to float within the member 2502 until the piston settles at a stable location with respect to the bearings 81 where least amount of forces act upon the piston. The bearings 81 can also be coated with an abradable material. The abradable material minimizes friction between the piston and the bearings, thereby eliminating the need for another lubricant to lubricate the piston and the plurality of bearings.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary implementations and implementations, it should be understood that the various features and functionality described in one or more of the individual implementations with which they are described, but instead can be applied, alone or in some combination, to one or more of the other implementations of the invention, whether or not such implementations are described and whether or not such features are presented as being a part of a described implementation. Thus the breadth and scope of the present invention, especially in any following claims, should not be limited by any of the above-described exemplary implementations.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary implementations of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some implementations shall not be read to mean that the narrower case is intended or required in implementations where such broadening phrases may be absent.

The invention claimed is:

1. A system comprising:
   a first inlet configured to receive fluid that is to be compressed;
   a first piston coated with abradable coating, the first piston configured to rotate around a first eccentric of a shaft in an orbital fashion in order to compress the fluid, the fluid being used as a lubricant for lubricating the first piston, the use of the fluid for lubricating and the abradable coating eliminating a need of another lubricant for lubricating the first piston;
   a first outlet configured to discharge the compressed fluid;
   a second inlet configured to receive, from a separator device, exhaust gases that have been separated from the fluid, the one or more gases being a subset of gases forming the fluid;
   a second piston coated with the abradable coating, the second piston configured to rotate around a second eccentric of the shaft in the orbital fashion, axial surfaces of the second piston being parallel to axial surfaces of the first piston, the exhaust gases being used as a lubricant for lubricating the second piston, the use of the exhaust gases for lubricating and the abradable coating of the second piston eliminating a need of another lubricant for lubricating the second piston; and
   a second outlet configured to exhaust the gases;
   wherein locations of at least one of the first inlet and the second inlet are moved to adjust timing of beginning of compression cycle for compressing the fluid.

2. The system of claim 1, further comprising:
   a first vane connected to the first piston;
   a first set of bushings slidingly connected to the first vane; and
   a first stator configured to enclose the first piston and the first vane.

3. The system of claim 2, wherein each bushing of the a first set of bushings has a flat surface in contact with a surface of the first vane.

4. The system of claim 2, wherein the first stator encloses a chamber that includes at least a vane chamber and a bore chamber, the bore chamber comprising a compression chamber and a suction chamber that is sealed from the compression chamber by the first vane and the first set of bushings.

5. The system of claim 4, wherein the compression chamber and the suction chamber are interchanged during the rotation of the first piston such that the compression chamber performs suction and the suction chamber performs compression.

6. The system of claim 1, further comprising:
   a suction endplate that incorporates the first inlet; and
   a discharge endplate that incorporates the first outlet.

7. The system of claim 6, wherein at least one of the first stator, the suction endplate and the discharge endplate are coated with the abradable coating.

8. The system of claim 7, wherein the abradable coating minimizes friction between the first piston and the first stator, the minimized friction between the first piston and the first stator eliminating the need of another lubricant for lubricating the first piston.

9. The system of claim 1, wherein the abradable coating comprises one of paint and a polymer based coating.

10. The system of claim 1, wherein the fluid that is to be compressed is ambient air, the ambient air being received at the first inlet from an ambient air collecting source.

11. The system of claim 10, wherein the ambient air comprises oxygen, nitrogen, and argon.

12. The system of claim 11, wherein the compressed fluid is pressurized ambient air, the pressurized air going from the first outlet to a separator device that separates the pressurized air into the oxygen, the nitrogen, and the argon.

13. The system of claim 12, wherein the separator device is a vacuum-pressure-swing-adsorption (VPSA) device.

14. The system of claim 12, wherein the separator device is a pressure-swing-adsorption (PSA) device.

15. The system of claim 12, wherein the separator device is a vacuum-swing-adsorption (VSA) device.

16. The system of claim 1, wherein an inner radial surface of the first piston is connected to an outside surface of the first eccentric by a plurality of bearings, the plurality of bearings configured to float underneath the first piston until the piston is at a stable location with respect to the plurality of bearings where least amount of forces act upon the piston.

17. The system of claim 16, wherein the plurality of bearings are rolling bearings.

18. A system comprising:
   a first inlet configured to receive fluid that is to be compressed;
   a first piston coated with abradable coating, the first piston configured to rotate around a first eccentric of a shaft in an orbital fashion in order to compress the fluid, the fluid being used as a lubricant for lubricating the first piston, the use of the fluid for lubricating and the abradable coating eliminating a need of another lubricant for lubricating the first piston;
   a first outlet configured to discharge the compressed fluid;
   a second inlet configured to receive, from a separator device, exhaust gases that have been separated from the fluid, the one or more gases being a subset of gases forming the fluid;

a second piston coated with the abradable coating, the second piston configured to rotate around a second eccentric of the shaft in the orbital fashion, axial surfaces of the second piston being parallel to axial surfaces of the first piston, the exhaust gases being used as a lubricant for lubricating the second piston, the use of the exhaust gases for lubricating and the abradable coating of the second piston eliminating a need of another lubricant for lubricating the second piston;

a second outlet configured to exhaust the gases;

a second vane connected to the second piston;

a second set of bushings slidingly connected to the second vane; and a second stator configured to enclose the second piston and the second vane, the first stator and the second stator being a single machined unit.

\* \* \* \* \*